(12) United States Patent
Buck et al.

(10) Patent No.: US 11,633,272 B2
(45) Date of Patent: Apr. 25, 2023

(54) MANUALLY ROTATABLE THROMBUS ENGAGEMENT TOOL

(71) Applicant: Imperative Care, Inc., Campbell, CA (US)

(72) Inventors: Michael Buck, Menlo Park, CA (US); Julia Fox, San Carlos, CA (US); James Jacobs, Danville, CA (US)

(73) Assignee: Imperative Care, Inc., Campbell, CA (US)

( * ) Notice: Subject to any disclaimer, the term of this patent is extended or adjusted under 35 U.S.C. 154(b) by 0 days.

(21) Appl. No.: 17/857,649

(22) Filed: Jul. 5, 2022

(65) Prior Publication Data

US 2022/0331085 A1 Oct. 20, 2022

Related U.S. Application Data

(63) Continuation-in-part of application No. 17/357,490, filed on Jun. 24, 2021, now Pat. No. 11,457,936, (Continued)

(51) Int. Cl.
*A61F 2/01* (2006.01)
*A61B 17/32* (2006.01)

(52) U.S. Cl.
CPC ..... *A61F 2/011* (2020.05); *A61B 2017/320032* (2013.01); *A61F 2230/0006* (2013.01); *A61F 2250/0098* (2013.01)

(58) Field of Classification Search
CPC .............. A61F 2/011; A61F 2230/0006; A61F 2250/0098; A61B 2017/320032; A61B 2018/0041
See application file for complete search history.

(56) References Cited

U.S. PATENT DOCUMENTS

| 3,605,750 A | 9/1971 | Sheridan et al. |
| 3,884,242 A | 5/1975 | Bazell et al. |

(Continued)

FOREIGN PATENT DOCUMENTS

| CN | 101123918 A | 2/2008 |
| CN | 101252958 A | 8/2008 |

(Continued)

OTHER PUBLICATIONS

Abay et al., 2014, Investigation of photoplethysmography and Near Infrared Spectroscopy for the assessment of tissue blood perfusion, 36th Annual International Conference of the IEEE Engineering in Medicine and Biology Society, Chicago, IL, pp. 5361-5364, doi: 10.1109/EMBC.2014.6944837.

(Continued)

*Primary Examiner* — Amber R Stiles
(74) *Attorney, Agent, or Firm* — Knobbe, Martens, Olson & Bear, LLP

(57) ABSTRACT

A thrombus engagement tool having a flexible shaft, a clot engagement tip, and a handle. The engagement tip may include one or more radially outwardly extending structures such as a helical thread. The helical thread can be advanced through a catheter to engage a clot. The handle may be configured to be rotated by hand. When the handle is rotated, the helical thread of the engagement tip can rotate in the same direction thereby allowing the helical threat to engage the clot. The helical thread can wrap around the flexible shaft at least about one, two, or four or more full revolutions, but in some cases no more than about ten or no more than about six revolutions.

35 Claims, 11 Drawing Sheets

Related U.S. Application Data which is a continuation-in-part of application No. 17/125,723, filed on Dec. 17, 2020, now Pat. No. 11,065,018.

(60) Provisional application No. 63/341,926, filed on May 13, 2022, provisional application No. 63/064,273, filed on Aug. 11, 2020, provisional application No. 63/044,511, filed on Jun. 26, 2020, provisional application No. 62/950,058, filed on Dec. 18, 2019.

(56) References Cited

U.S. PATENT DOCUMENTS

| | | |
|---|---|---|
| 3,890,976 A | 6/1975 | Bazell et al. |
| 3,965,901 A | 6/1976 | Penny et al. |
| 4,030,503 A * | 6/1977 | Clark, III ............ A61B 17/3207 |
| | | 606/159 |
| 4,319,580 A | 3/1982 | Colley et al. |
| 4,611,594 A | 9/1986 | Grayhack et al. |
| 4,617,019 A | 10/1986 | Fecht et al. |
| 4,619,274 A | 10/1986 | Morrison |
| 4,628,168 A | 12/1986 | Nebergall et al. |
| 4,762,129 A | 8/1988 | Bonzel |
| 4,762,130 A | 8/1988 | Fogarty et al. |
| 4,767,399 A | 8/1988 | Bollish |
| 4,810,582 A | 3/1989 | Gould et al. |
| 4,844,064 A | 7/1989 | Thimsen et al. |
| 4,898,575 A | 2/1990 | Fischell et al. |
| 4,923,462 A | 5/1990 | Stevens |
| 5,011,488 A | 4/1991 | Ginsburg |
| 5,040,548 A | 8/1991 | Yock |
| 5,103,827 A | 4/1992 | Smith |
| 5,120,323 A | 6/1992 | Shockey et al. |
| 5,217,705 A | 6/1993 | Reno et al. |
| 5,226,909 A | 7/1993 | Evans et al. |
| 5,234,416 A | 8/1993 | Macaulay et al. |
| 5,243,997 A | 9/1993 | Uflacker et al. |
| 5,261,916 A | 11/1993 | Engelson et al. |
| 5,290,247 A | 3/1994 | Crittenden |
| 5,308,327 A | 5/1994 | Heaven et al. |
| 5,328,472 A | 7/1994 | Steinke et al. |
| 5,413,560 A | 5/1995 | Solar |
| 5,417,697 A | 5/1995 | Wilk et al. |
| 5,423,846 A | 6/1995 | Fischell |
| 5,439,445 A | 8/1995 | Kontos |
| 5,441,051 A | 8/1995 | Hileman et al. |
| 5,454,795 A | 10/1995 | Samson |
| 5,466,222 A | 11/1995 | Ressemann et al. |
| 5,474,563 A | 12/1995 | Myler et al. |
| 5,527,292 A | 6/1996 | Adams et al. |
| 5,549,119 A | 8/1996 | Solar |
| 5,569,178 A | 10/1996 | Henley |
| 5,569,277 A | 10/1996 | Evans et al. |
| 5,591,187 A | 1/1997 | Dekel |
| 5,643,254 A | 7/1997 | Scheldrup et al. |
| 5,658,263 A | 8/1997 | Dang et al. |
| 5,662,622 A | 9/1997 | Gore et al. |
| 5,690,613 A | 11/1997 | Verbeek |
| 5,695,483 A | 12/1997 | Samson |
| 5,702,373 A | 12/1997 | Samson |
| 5,713,848 A | 2/1998 | Dubrul et al. |
| 5,766,191 A | 6/1998 | Trerotola |
| 5,776,141 A | 7/1998 | Klein et al. |
| 5,792,124 A | 8/1998 | Horrigan et al. |
| 5,827,242 A | 10/1998 | Follmer et al. |
| 5,843,103 A | 12/1998 | Wulfman |
| 5,873,882 A | 2/1999 | Straub et al. |
| 5,876,414 A | 3/1999 | Straub |
| 5,885,209 A | 3/1999 | Green |
| 5,891,114 A | 4/1999 | Chien et al. |
| 5,895,398 A | 4/1999 | Wensel et al. |
| 5,899,892 A | 5/1999 | Mortier et al. |
| 5,916,192 A | 6/1999 | Nita et al. |
| 5,935,112 A | 8/1999 | Stevens |
| 5,938,645 A | 8/1999 | Gordon |
| 5,951,539 A | 9/1999 | Nita |
| 6,007,530 A | 12/1999 | Dornhofer et al. |
| 6,056,837 A | 5/2000 | Lieber et al. |
| 6,059,745 A | 5/2000 | Gelbfish |
| 6,090,118 A | 7/2000 | McGuckin, Jr. |
| 6,152,909 A | 11/2000 | Bagaoisan et al. |
| 6,159,230 A | 12/2000 | Samuels |
| 6,165,163 A | 12/2000 | Chien et al. |
| 6,165,199 A | 12/2000 | Barbut |
| 6,171,295 B1 | 1/2001 | Garabedian et al. |
| 6,179,859 B1 | 1/2001 | Bates et al. |
| 6,197,014 B1 | 3/2001 | Samson et al. |
| 6,206,852 B1 | 3/2001 | Lee |
| 6,217,557 B1 | 4/2001 | Hakansson et al. |
| 6,221,038 B1 | 4/2001 | Brisken |
| 6,228,046 B1 | 5/2001 | Brisken |
| 6,258,052 B1 | 7/2001 | Milo |
| 6,267,783 B1 | 7/2001 | Letendre et al. |
| 6,285,903 B1 | 9/2001 | Rosenthal et al. |
| 6,355,027 B1 | 3/2002 | Le et al. |
| 6,394,976 B1 | 5/2002 | Winston et al. |
| 6,451,036 B1 | 6/2002 | Heitzmann et al. |
| 6,451,005 B1 | 9/2002 | Saitou et al. |
| 6,458,139 B1 | 10/2002 | Palmer et al. |
| 6,468,219 B1 | 10/2002 | Njemanze |
| 6,482,217 B1 | 11/2002 | Pintor et al. |
| 6,511,492 B1 | 1/2003 | Rosenbluth et al. |
| 6,524,303 B1 | 2/2003 | Garibaldi et al. |
| 6,520,934 B1 | 3/2003 | Lee et al. |
| 6,533,751 B2 | 3/2003 | Cragg et al. |
| 6,554,820 B1 | 4/2003 | Wendlandt et al. |
| 6,554,827 B2 | 4/2003 | Chandrasekaran et al. |
| 6,558,377 B2 | 5/2003 | Lee et al. |
| 6,569,148 B2 | 5/2003 | Bagaoisan et al. |
| 6,579,246 B2 | 6/2003 | Jacobsen et al. |
| 6,582,440 B1 | 6/2003 | Brumbach |
| 6,591,472 B1 | 7/2003 | Noone et al. |
| 6,638,268 B2 | 10/2003 | Niazi |
| 6,663,613 B1 | 12/2003 | Evans et al. |
| 6,666,874 B2 | 12/2003 | Heitzmann |
| 6,669,670 B1 | 12/2003 | Muni et al. |
| 6,719,717 B1 | 4/2004 | Johnson et al. |
| 6,776,770 B1 | 8/2004 | Trerotola |
| 6,805,692 B2 | 10/2004 | Muni et al. |
| 6,824,550 B1 | 11/2004 | Pintor et al. |
| 6,824,553 B1 | 11/2004 | Samson et al. |
| 6,977,068 B1 | 12/2005 | Nair et al. |
| 7,004,954 B1 | 2/2006 | Voss et al. |
| 7,008,434 B2 | 3/2006 | Kurz et al. |
| 7,029,482 B1 | 4/2006 | Vargas et al. |
| 7,037,267 B1 | 5/2006 | Lipson et al. |
| 7,104,979 B2 | 9/2006 | Jansen et al. |
| 7,112,298 B2 | 9/2006 | Kampa et al. |
| 7,172,620 B2 | 2/2007 | Gilson |
| 7,175,653 B2 | 2/2007 | Gaber |
| 7,207,980 B2 | 4/2007 | Christian et al. |
| 7,223,274 B2 | 5/2007 | Vargas et al. |
| 7,229,461 B2 | 6/2007 | Chin et al. |
| 7,232,452 B2 | 6/2007 | Adams et al. |
| 7,235,088 B2 | 6/2007 | Pintor et al. |
| 7,250,042 B2 | 7/2007 | Kataishi et al. |
| 7,306,585 B2 | 12/2007 | Ross |
| 7,309,334 B2 | 12/2007 | von Hoffmann |
| 7,335,216 B2 | 2/2008 | Bender et al. |
| 7,416,555 B2 | 8/2008 | Krivoruchko |
| 7,491,210 B2 | 2/2009 | Dubrul et al. |
| 7,507,229 B2 | 3/2009 | Hewitt et al. |
| 7,537,568 B2 | 5/2009 | Moehring |
| 7,558,622 B2 | 7/2009 | Tran |
| 7,601,138 B2 | 10/2009 | Goebel et al. |
| 7,678,100 B2 | 3/2010 | Chin et al. |
| 7,713,227 B2 | 5/2010 | Wholey et al. |
| 7,763,196 B2 | 7/2010 | Goebel et al. |
| 7,766,871 B2 | 8/2010 | Hirszowicz et al. |
| 7,771,358 B2 | 8/2010 | Moehring et al. |
| 7,803,136 B2 | 9/2010 | Schatz |
| 7,837,692 B2 | 11/2010 | Mulholland et al. |
| 7,842,055 B2 | 11/2010 | Pintor et al. |
| 7,850,623 B2 | 12/2010 | Griffin et al. |

(56) References Cited

U.S. PATENT DOCUMENTS

| | | |
|---|---|---|
| 7,905,891 B2 | 3/2011 | Self |
| 7,931,659 B2 | 4/2011 | Bose et al. |
| 7,938,820 B2 | 5/2011 | Webster et al. |
| 7,947,012 B2 | 5/2011 | Spurchise et al. |
| 7,955,344 B2 | 6/2011 | Finitsis |
| 7,955,345 B2 | 6/2011 | Kucharczyk et al. |
| 7,988,646 B2 | 8/2011 | Taber |
| 8,021,351 B2 | 9/2011 | Boldenow et al. |
| 8,048,032 B2 | 11/2011 | Root et al. |
| 8,057,497 B1 | 11/2011 | Raju et al. |
| 8,062,316 B2 | 11/2011 | Patel et al. |
| 8,070,694 B2 | 12/2011 | Galdonik et al. |
| 8,079,978 B2 | 12/2011 | Hirszowicz et al. |
| 8,084,246 B2 | 12/2011 | Hoon et al. |
| 8,114,106 B2 | 2/2012 | Straub |
| 8,123,769 B2 | 2/2012 | Osborne |
| 8,142,413 B2 | 3/2012 | Root et al. |
| 8,114,032 B2 | 4/2012 | Ferry et al. |
| 8,157,792 B2 | 4/2012 | Dolliver et al. |
| 8,211,023 B2 | 7/2012 | Swan et al. |
| 8,235,968 B2 | 8/2012 | Tremaglio |
| 8,246,641 B2 | 8/2012 | Osborne et al. |
| 8,292,850 B2 | 10/2012 | Root et al. |
| 8,298,591 B2 | 10/2012 | Srivastava et al. |
| 8,308,655 B2 | 11/2012 | Grigoryants |
| 8,361,095 B2 | 1/2013 | Osborne |
| 8,366,735 B2 | 2/2013 | Bose et al. |
| 8,382,739 B2 | 2/2013 | Walak et al. |
| 8,394,078 B2 | 3/2013 | Torrance et al. |
| 8,403,912 B2 | 3/2013 | McFerran et al. |
| 8,419,748 B2 | 4/2013 | Valaie |
| 8,449,566 B2 | 5/2013 | Finitsis |
| 8,460,312 B2 | 6/2013 | Bose et al. |
| 8,480,697 B2 | 7/2013 | Kucharczyk et al. |
| 8,485,969 B2 | 7/2013 | Grayzel et al. |
| 8,506,555 B2 | 8/2013 | Morales |
| 8,517,955 B2 | 8/2013 | Keast et al. |
| 8,535,293 B2 | 9/2013 | Faherty et al. |
| 8,568,432 B2 | 10/2013 | Straub |
| 8,603,122 B2 | 12/2013 | Pokorney et al. |
| 8,608,754 B2 | 12/2013 | Wensel et al. |
| 8,608,761 B2 | 12/2013 | Osborne et al. |
| 8,609,426 B2 | 12/2013 | Silver |
| 8,663,259 B2 | 3/2014 | Levine et al. |
| 8,682,411 B2 | 3/2014 | Kassab et al. |
| 8,684,963 B2 | 4/2014 | Qiu et al. |
| 8,696,698 B2 | 4/2014 | Chomas et al. |
| 8,702,680 B2 | 4/2014 | Jimenez et al. |
| 8,702,724 B2 | 4/2014 | Olsen et al. |
| 8,725,249 B2 | 5/2014 | Bar-Yoseph et al. |
| 8,734,374 B2 | 5/2014 | Aklog et al. |
| 8,758,325 B2 | 6/2014 | Webster et al. |
| 8,758,364 B2 | 6/2014 | Eckhouse et al. |
| 8,764,779 B2 | 7/2014 | Levine et al. |
| 8,784,441 B2 | 7/2014 | Rosenbluth et al. |
| 8,814,892 B2 | 8/2014 | Galdonik et al. |
| 8,864,792 B2 | 10/2014 | Eckhouse et al. |
| 8,876,854 B2 | 11/2014 | Christiansen et al. |
| 8,900,257 B2 | 12/2014 | Straub et al. |
| 8,932,320 B1 | 1/2015 | Janardhan et al. |
| RE45,380 E | 2/2015 | Root et al. |
| 8,968,383 B1 | 3/2015 | Johnson et al. |
| 8,974,411 B2 | 3/2015 | McKinnon |
| 8,992,506 B2 | 3/2015 | Gulachenski |
| 8,996,095 B2 | 3/2015 | Anderson et al. |
| 8,998,946 B2 | 4/2015 | Morero |
| 9,005,237 B2 | 4/2015 | Eckhouse et al. |
| 9,014,786 B2 | 4/2015 | Carmeli et al. |
| 9,017,309 B2 | 4/2015 | Tanikawa et al. |
| 9,023,070 B2 | 5/2015 | Levine et al. |
| 9,034,008 B2 | 5/2015 | Eckhouse et al. |
| 9,039,715 B2 | 5/2015 | Diamant et al. |
| 9,079,000 B2 | 7/2015 | Hanson et al. |
| 9,107,691 B2 | 8/2015 | Fojtik |
| 9,119,625 B2 | 9/2015 | Bachman et al. |
| 9,119,656 B2 | 9/2015 | Bose et al. |
| 9,138,307 B2 | 9/2015 | Valaie |
| 9,144,383 B2 | 9/2015 | Zharov |
| 9,144,662 B2 | 9/2015 | DiCaprio et al. |
| RE45,760 E | 10/2015 | Root et al. |
| RE45,776 E | 10/2015 | Root et al. |
| 9,199,064 B2 | 12/2015 | Morero |
| 9,211,396 B2 | 12/2015 | Aboytes |
| 9,238,124 B2 | 1/2016 | Grayzel et al. |
| 9,241,699 B1 | 1/2016 | Kume et al. |
| 9,259,215 B2 | 2/2016 | Chou et al. |
| 9,259,228 B2 | 2/2016 | Cruise et al. |
| 9,265,512 B2 | 2/2016 | Garrison et al. |
| 9,278,201 B2 | 3/2016 | Rapaport et al. |
| 9,282,992 B2 | 3/2016 | Levine et al. |
| 9,295,817 B2 | 3/2016 | Chang |
| 9,314,268 B2 | 4/2016 | Cahill |
| 9,339,282 B2 | 5/2016 | Green et al. |
| 9,345,508 B2 | 5/2016 | Hendrick |
| 9,345,856 B2 | 5/2016 | Witte |
| 9,351,993 B2 | 5/2016 | Cruise et al. |
| 9,370,639 B2 | 6/2016 | Plassman et al. |
| 9,375,223 B2 | 6/2016 | Wallace |
| 9,381,278 B2 | 7/2016 | Constant et al. |
| 9,398,946 B2 | 7/2016 | Valaie |
| 9,399,118 B2 | 7/2016 | Kume et al. |
| RE46,116 E | 8/2016 | Root et al. |
| 9,408,916 B2 | 8/2016 | Cruise et al. |
| 9,414,819 B2 | 8/2016 | Fitz et al. |
| 9,421,328 B2 | 8/2016 | Brueckner et al. |
| 9,439,791 B2 | 9/2016 | Vong et al. |
| 9,440,018 B2 | 9/2016 | Levin et al. |
| 9,446,216 B2 | 9/2016 | Olesky et al. |
| 9,451,884 B2 | 9/2016 | Palovich et al. |
| 9,451,963 B2 | 9/2016 | Cruise et al. |
| 9,463,006 B2 | 10/2016 | Forde et al. |
| 9,480,813 B2 | 11/2016 | Fukuoka et al. |
| 9,486,221 B2 | 11/2016 | Cruise et al. |
| 9,492,637 B2 | 11/2016 | Garrison et al. |
| 9,504,476 B2 | 11/2016 | Gulachenski |
| 9,510,855 B2 | 12/2016 | Rapaport et al. |
| 9,526,504 B2 | 12/2016 | Chang |
| 9,526,505 B2 | 12/2016 | Marks et al. |
| 9,532,792 B2 | 1/2017 | Galdonik et al. |
| 9,533,344 B2 | 1/2017 | Monetti et al. |
| 9,539,022 B2 | 1/2017 | Bowman |
| 9,539,122 B2 | 1/2017 | Burke et al. |
| 9,546,236 B2 | 1/2017 | Cruise et al. |
| 9,561,121 B2 | 2/2017 | Sudin et al. |
| 9,561,125 B2 | 2/2017 | Bowman et al. |
| 9,561,345 B2 | 2/2017 | Garrison et al. |
| 9,597,101 B2 | 3/2017 | Galdonik et al. |
| 9,597,212 B2 | 3/2017 | Thompson et al. |
| 9,615,832 B2 | 3/2017 | Bose et al. |
| 9,622,753 B2 | 4/2017 | Cox |
| 9,623,228 B2 | 4/2017 | Ryan et al. |
| 9,655,633 B2 | 5/2017 | Leynov et al. |
| 9,655,755 B2 | 5/2017 | Chou et al. |
| 9,655,989 B2 | 5/2017 | Cruise et al. |
| 9,662,118 B2 | 5/2017 | Chang |
| 9,662,129 B2 | 5/2017 | Galdonik et al. |
| 9,662,480 B2 | 5/2017 | Kume et al. |
| 9,669,183 B2 | 6/2017 | Chang |
| 9,669,191 B2 | 6/2017 | Chou et al. |
| 9,681,882 B2 | 6/2017 | Garrison et al. |
| 9,688,788 B2 | 6/2017 | Plotkin et al. |
| 9,693,789 B2 | 7/2017 | Garrison et al. |
| 9,693,852 B2 | 7/2017 | Lam et al. |
| 9,707,380 B2 | 7/2017 | Qiu et al. |
| 9,717,500 B2 | 8/2017 | Tieu et al. |
| 9,724,103 B2 | 8/2017 | Cruise et al. |
| 9,724,491 B2 | 8/2017 | Solar et al. |
| 9,764,111 B2 | 9/2017 | Gulachenski |
| 9,770,251 B2 | 9/2017 | Bowman et al. |
| 9,775,730 B1 | 10/2017 | Waltzman |
| 9,789,242 B2 | 10/2017 | Criado et al. |
| 9,789,283 B2 | 10/2017 | Richter et al. |
| 9,801,643 B2 | 10/2017 | Hansen et al. |
| 9,803,043 B2 | 10/2017 | Cruise et al. |

(56) References Cited

U.S. PATENT DOCUMENTS

| | | |
|---|---|---|
| 9,808,610 B2 | 11/2017 | Li et al. |
| 9,820,761 B2 | 11/2017 | Garrison et al. |
| 9,827,047 B2 | 11/2017 | Fudaba et al. |
| 9,828,157 B2 | 11/2017 | Roesler |
| 9,855,072 B2 | 1/2018 | Moberg et al. |
| 9,861,783 B2 | 1/2018 | Garrison et al. |
| 9,877,731 B2 | 1/2018 | Cruise et al. |
| 9,877,742 B2 | 1/2018 | Milner et al. |
| 9,878,076 B2 | 1/2018 | Gülcher et al. |
| 9,883,885 B2 | 2/2018 | Hendrick et al. |
| 9,907,880 B2 | 3/2018 | Cruise et al. |
| 9,913,960 B2 | 3/2018 | Blanchard et al. |
| 9,931,129 B2 | 4/2018 | Walish et al. |
| 9,943,321 B2 | 4/2018 | Nita |
| 9,987,027 B2 | 6/2018 | Ben-Ami |
| 9,987,028 B2 | 6/2018 | Lowinger et al. |
| 9,999,355 B2 | 6/2018 | Kirenko |
| 10,010,698 B2 | 7/2018 | Watanabe et al. |
| 10,028,854 B2 | 7/2018 | Tatalovich et al. |
| 10,039,906 B2 | 8/2018 | Kume et al. |
| 10,052,761 B2 | 8/2018 | Langenfeld et al. |
| 10,070,878 B2 | 9/2018 | Ma |
| 10,086,169 B2 | 10/2018 | Grayzel et al. |
| 10,105,154 B1 | 10/2018 | Green |
| 10,179,224 B2 | 1/2019 | Yang et al. |
| 10,183,145 B2 | 1/2019 | Yang et al. |
| 10,183,146 B2 | 1/2019 | Yang et al. |
| 10,183,147 B2 | 1/2019 | Yang et al. |
| 10,207,077 B2 | 2/2019 | Griggin et al. |
| 10,213,582 B2 | 2/2019 | Garrison et al. |
| 10,226,277 B2 | 3/2019 | Smith et al. |
| 10,238,833 B2 | 3/2019 | Christian et al. |
| 10,258,452 B2 | 4/2019 | Eckhouse et al. |
| 10,265,086 B2 | 4/2019 | Vale |
| 10,271,864 B2 | 4/2019 | Greenhalgh et al. |
| RE47,376 E | 5/2019 | Pokorney et al. |
| 10,278,678 B2 | 5/2019 | Peliks |
| 10,278,816 B2 | 5/2019 | Miller |
| 10,300,256 B2 | 5/2019 | Aboytes |
| 10,327,790 B2 | 6/2019 | Garrison et al. |
| 10,335,186 B2 | 7/2019 | Rosenbluth et al. |
| 10,342,570 B2 | 7/2019 | Richter et al. |
| 10,383,691 B2 | 8/2019 | Hendrick et al. |
| 10,383,751 B2 | 8/2019 | Ferrera et al. |
| 10,384,034 B2 | 8/2019 | Garrison et al. |
| 10,420,581 B2 | 9/2019 | Hehrlein |
| 10,441,745 B2 | 10/2019 | Yang et al. |
| 10,456,552 B2 | 10/2019 | Goyal |
| 10,471,233 B2 | 11/2019 | Garrison et al. |
| 10,524,814 B2 | 1/2020 | Chang et al. |
| 10,531,883 B1 | 1/2020 | Deville et al. |
| 10,537,706 B2 | 1/2020 | Kanemasa et al. |
| 10,569,049 B2 | 2/2020 | Garrison et al. |
| 10,610,256 B2 | 4/2020 | Bowman |
| 10,610,668 B2 | 4/2020 | Burkholz et al. |
| 10,646,239 B2 | 5/2020 | Garrison et al. |
| 10,653,426 B2 | 5/2020 | Yang et al. |
| 10,653,434 B1 | 5/2020 | Yang et al. |
| 10,661,053 B2 | 5/2020 | Yang et al. |
| 10,668,192 B2 | 6/2020 | Raney et al. |
| 10,695,159 B2 | 6/2020 | Hauser |
| 10,716,880 B2 | 7/2020 | Culbert et al. |
| 10,716,915 B2 | 7/2020 | Ogle et al. |
| 10,722,251 B2 | 7/2020 | Garrison et al. |
| 10,722,253 B2 | 7/2020 | Deville et al. |
| 10,722,683 B2 | 7/2020 | Solar et al. |
| 10,743,893 B2 | 8/2020 | Garrison et al. |
| 10,751,073 B2 | 8/2020 | Eckhouse et al. |
| 10,772,647 B2 | 9/2020 | Ben-Ami |
| 10,786,268 B2 | 9/2020 | Ben-Ami |
| 10,786,270 B2 | 9/2020 | Yang et al. |
| 10,792,056 B2 | 10/2020 | Vale et al. |
| 10,835,272 B2 | 11/2020 | Yang et al. |
| 10,835,278 B2 | 11/2020 | Wilke et al. |
| 10,835,711 B2 | 11/2020 | Yang et al. |
| 10,856,898 B2 | 12/2020 | Matsushita et al. |
| 10,888,280 B2 | 1/2021 | Newberry |
| 10,905,850 B2 | 2/2021 | Christian et al. |
| 11,020,030 B2 | 6/2021 | Tao et al. |
| 11,020,059 B2 | 6/2021 | Sheth et al. |
| 11,039,845 B2 | 6/2021 | Wallace |
| 11,065,018 B2 | 7/2021 | Buck et al. |
| 11,076,876 B2 | 8/2021 | Vale |
| 11,123,090 B2 | 9/2021 | Yang et al. |
| 11,134,859 B2 | 10/2021 | Strasser |
| 11,147,949 B2 | 10/2021 | Yang et al. |
| 11,197,683 B1 | 12/2021 | Teigen et al. |
| 11,197,771 B2 | 12/2021 | Ferrera et al. |
| 11,207,096 B2 | 12/2021 | To et al. |
| 11,207,497 B1 | 12/2021 | Yee et al. |
| 11,224,434 B2 | 1/2022 | Yang et al. |
| 11,224,457 B2 | 1/2022 | Brinkmann et al. |
| 11,243,277 B2 | 2/2022 | Buck et al. |
| 11,253,292 B2 | 2/2022 | McGuckin, Jr. et al. |
| 11,259,821 B2 | 3/2022 | Buck et al. |
| 11,311,303 B2 | 4/2022 | Yang et al. |
| 11,395,665 B2 | 7/2022 | Yang et al. |
| 11,439,799 B2 | 9/2022 | Buck et al. |
| 11,457,936 B2 | 10/2022 | Buck et al. |
| 11,471,582 B2 | 10/2022 | Yee |
| 2001/0031980 A1 | 10/2001 | Wensel et al. |
| 2001/0031981 A1 | 10/2001 | Evans et al. |
| 2001/0049486 A1 | 12/2001 | Evans et al. |
| 2002/0016565 A1 | 2/2002 | Zadno-Azizi et al. |
| 2002/0026145 A1 | 2/2002 | Bagaoisan et al. |
| 2002/0074276 A1 | 6/2002 | Nakashima |
| 2002/0091372 A1 | 7/2002 | Cragg et al. |
| 2002/0156459 A1 | 10/2002 | Ye et al. |
| 2002/0156460 A1 | 10/2002 | Ye et al. |
| 2002/0169467 A1 | 11/2002 | Heitzmann et al. |
| 2002/0173812 A1 | 11/2002 | McGuckin et al. |
| 2002/0177899 A1 | 11/2002 | Eum et al. |
| 2002/0188314 A1 | 12/2002 | Anderson et al. |
| 2003/0088266 A1 | 5/2003 | Bowlin |
| 2003/0135193 A1 | 7/2003 | Hilgers et al. |
| 2003/0135198 A1 | 7/2003 | Berhow et al. |
| 2003/0153847 A1 | 8/2003 | Sandler et al. |
| 2003/0153874 A1 | 8/2003 | Tal |
| 2003/0195467 A1 | 10/2003 | Mickley |
| 2003/0195546 A1 | 10/2003 | Solar et al. |
| 2003/0225336 A1 | 12/2003 | Callister et al. |
| 2004/0010280 A1 | 1/2004 | Adams et al. |
| 2004/0059290 A1 | 3/2004 | Palasis |
| 2004/0138693 A1 | 7/2004 | Eskuri et al. |
| 2004/0153049 A1 | 8/2004 | Hewitt et al. |
| 2004/0199201 A1 | 10/2004 | Kellett et al. |
| 2004/0215222 A1 | 10/2004 | Krivoruchko |
| 2004/0236215 A1 | 11/2004 | Mihara et al. |
| 2004/0243102 A1 | 12/2004 | Berg et al. |
| 2005/0004523 A1 | 1/2005 | Osborne et al. |
| 2005/0004553 A1 | 1/2005 | Douk |
| 2005/0021002 A1 | 1/2005 | Deckman et al. |
| 2005/0055047 A1 | 3/2005 | Greenhalgh |
| 2005/0059957 A1 | 3/2005 | Campbell et al. |
| 2005/0080400 A1 | 4/2005 | Corcoran et al. |
| 2005/0103332 A1 | 5/2005 | Gingles et al. |
| 2005/0124985 A1 | 6/2005 | Takayama et al. |
| 2005/0137680 A1 | 6/2005 | Ortiz et al. |
| 2005/0182386 A1 | 8/2005 | Aggerholm |
| 2005/0187570 A1 | 8/2005 | Nguyen et al. |
| 2005/0228417 A1 | 10/2005 | Teitelbaum |
| 2006/0020285 A1 | 1/2006 | Niermann |
| 2006/0020286 A1 | 1/2006 | Niermann |
| 2006/0030835 A1 | 2/2006 | Sherman et al. |
| 2006/0064036 A1 | 3/2006 | Osborne et al. |
| 2006/0074401 A1 | 4/2006 | Ross |
| 2006/0089618 A1 | 4/2006 | McFerran et al. |
| 2006/0095062 A1 | 5/2006 | Stephens |
| 2006/0100530 A1 | 5/2006 | Kliot et al. |
| 2006/0111649 A1 | 5/2006 | Zhou |
| 2006/0124212 A1 | 6/2006 | Zhou |
| 2006/0149355 A1 | 7/2006 | Mitelberg et al. |
| 2006/0217664 A1 | 9/2006 | Hattler et al. |
| 2006/0247755 A1 | 11/2006 | Pal et al. |

(56) References Cited

U.S. PATENT DOCUMENTS

| | | |
|---|---|---|
| 2006/0264759 A1 | 11/2006 | Moehring et al. |
| 2007/0016132 A1 | 1/2007 | Oepen et al. |
| 2007/0038225 A1* | 2/2007 | Osborne ............. A61B 17/221 606/113 |
| 2007/0043333 A1 | 2/2007 | Kampa et al. |
| 2007/0060888 A1 | 3/2007 | Goff et al. |
| 2007/0185521 A1 | 8/2007 | Bui et al. |
| 2007/0197956 A1 | 8/2007 | Le et al. |
| 2007/0225614 A1 | 9/2007 | Naghavi et al. |
| 2007/0239182 A1 | 10/2007 | Glines et al. |
| 2008/0045881 A1 | 2/2008 | Teitelbaum et al. |
| 2008/0064984 A1 | 3/2008 | Pflueger et al. |
| 2008/0086110 A1 | 4/2008 | Galdonik et al. |
| 2008/0097251 A1 | 4/2008 | Babaev et al. |
| 2008/0188928 A1 | 8/2008 | Salahieh et al. |
| 2008/0234715 A1 | 9/2008 | Pesce |
| 2008/0262350 A1 | 10/2008 | Unger |
| 2008/0294058 A1 | 11/2008 | Shklarski |
| 2008/0300544 A1 | 12/2008 | Palm et al. |
| 2008/0312639 A1 | 12/2008 | Weber |
| 2009/0030400 A1 | 1/2009 | Bose et al. |
| 2009/0043330 A1 | 2/2009 | To |
| 2009/0093829 A1 | 4/2009 | Melsheimer et al. |
| 2009/0138031 A1 | 5/2009 | Tsukernik |
| 2009/0171368 A1 | 7/2009 | Pearce et al. |
| 2009/0182370 A1 | 7/2009 | Volobuyev et al. |
| 2009/0187143 A1 | 7/2009 | Vreeman |
| 2009/0209857 A1 | 8/2009 | Secretain et al. |
| 2009/0210048 A1 | 8/2009 | Amplatz et al. |
| 2009/0227992 A1 | 9/2009 | Nir et al. |
| 2009/0234321 A1 | 9/2009 | Shapland et al. |
| 2009/0264785 A1 | 10/2009 | Causevic et al. |
| 2009/0264865 A1 | 10/2009 | Kawai |
| 2009/0270800 A1 | 10/2009 | Spurchise et al. |
| 2009/0270888 A1 | 10/2009 | Patel et al. |
| 2009/0275974 A1 | 11/2009 | Marchand et al. |
| 2009/0287190 A1 | 11/2009 | Shippert |
| 2009/0312699 A1 | 12/2009 | Pudelko |
| 2010/0023033 A1 | 1/2010 | Mauch et al. |
| 2010/0030256 A1 | 2/2010 | Dubrul et al. |
| 2010/0049168 A1 | 2/2010 | Parker et al. |
| 2010/0057051 A1 | 3/2010 | Howat et al. |
| 2010/0114017 A1 | 5/2010 | Lenker et al. |
| 2010/0114022 A1 | 5/2010 | Hirszowicz et al. |
| 2010/0125253 A1 | 5/2010 | Olson et al. |
| 2010/0137793 A1 | 6/2010 | Hirszowicz et al. |
| 2010/0217235 A1 | 8/2010 | Thorstenson et al. |
| 2010/0217276 A1 | 8/2010 | Garrison et al. |
| 2010/0312141 A1 | 12/2010 | Keast et al. |
| 2010/0331916 A1 | 12/2010 | Parramon et al. |
| 2011/0009875 A1 | 1/2011 | Grandfield et al. |
| 2011/0034986 A1 | 2/2011 | Chou |
| 2011/0054504 A1 | 3/2011 | Porter |
| 2011/0077620 A1 | 3/2011 | deBeer |
| 2011/0082373 A1 | 4/2011 | Gurley et al. |
| 2011/0106200 A1 | 5/2011 | Ziegler |
| 2011/0137399 A1 | 6/2011 | Chomas et al. |
| 2011/0152920 A1 | 6/2011 | Eckhouse et al. |
| 2011/0152998 A1 | 6/2011 | Berez et al. |
| 2011/0172700 A1 | 7/2011 | Bose et al. |
| 2011/0178418 A1 | 7/2011 | Avidor et al. |
| 2011/0230859 A1 | 9/2011 | Galdonik et al. |
| 2011/0238041 A1 | 9/2011 | Lim et al. |
| 2011/0295217 A1 | 12/2011 | Tanaka et al. |
| 2012/0016407 A1 | 1/2012 | Sakai |
| 2012/0040858 A1 | 2/2012 | Ford et al. |
| 2012/0041474 A1 | 2/2012 | Eckhouse |
| 2012/0065479 A1 | 3/2012 | Lahiji et al. |
| 2012/0065490 A1 | 3/2012 | Zharov et al. |
| 2012/0078140 A1 | 3/2012 | Nita |
| 2012/0083868 A1 | 4/2012 | Shrivastava et al. |
| 2012/0123327 A1 | 5/2012 | Miller |
| 2012/0143237 A1 | 6/2012 | Cam et al. |
| 2012/0150147 A1 | 6/2012 | Leynov et al. |
| 2012/0259718 A1 | 10/2012 | Miller et al. |
| 2012/0290067 A1 | 11/2012 | Cam et al. |
| 2012/0296362 A1 | 11/2012 | Cam et al. |
| 2012/0330196 A1 | 12/2012 | Nita |
| 2013/0006225 A1 | 1/2013 | Cucin |
| 2013/0018318 A1 | 1/2013 | Ravichandran et al. |
| 2013/0018359 A1 | 1/2013 | Coyle |
| 2013/0030461 A1 | 1/2013 | Marks et al. |
| 2013/0035628 A1 | 2/2013 | Garrison et al. |
| 2013/0046285 A1 | 2/2013 | Griffin et al. |
| 2013/0046374 A1 | 2/2013 | Jones-McMeans |
| 2013/0116701 A1 | 5/2013 | Wang et al. |
| 2013/0131641 A1 | 5/2013 | Jimenez et al. |
| 2013/0131710 A1 | 5/2013 | Carmeli et al. |
| 2013/0144328 A1 | 6/2013 | Weber et al. |
| 2013/0158511 A1 | 6/2013 | Aggerholm et al. |
| 2013/0158578 A1 | 6/2013 | Ghodke et al. |
| 2013/0325055 A1 | 12/2013 | Eckhouse et al. |
| 2014/0025043 A1 | 1/2014 | Wang et al. |
| 2014/0046243 A1 | 2/2014 | Ray et al. |
| 2014/0046244 A1 | 2/2014 | Ray et al. |
| 2014/0074144 A1 | 3/2014 | Shrivastava et al. |
| 2014/0114287 A1 | 4/2014 | Beasley et al. |
| 2014/0118931 A1 | 5/2014 | Hata |
| 2014/0121555 A1 | 5/2014 | Scott et al. |
| 2014/0121746 A1 | 5/2014 | Kusleika et al. |
| 2014/0155932 A1 | 6/2014 | Bose et al. |
| 2014/0155980 A1 | 6/2014 | Turjman et al. |
| 2014/0163367 A1 | 6/2014 | Eskuri |
| 2014/0200608 A1 | 7/2014 | Brady et al. |
| 2014/0228808 A1 | 8/2014 | Webster et al. |
| 2014/0243882 A1 | 8/2014 | Ma |
| 2014/0249508 A1 | 9/2014 | Wang et al. |
| 2014/0273920 A1 | 9/2014 | Smith |
| 2014/0275832 A1 | 9/2014 | Muehlsteff et al. |
| 2014/0275852 A1 | 9/2014 | Hong et al. |
| 2014/0276167 A1 | 9/2014 | Dasgupta et al. |
| 2014/0276618 A1 | 9/2014 | Di Caprio et al. |
| 2014/0276920 A1 | 9/2014 | Hendrick et al. |
| 2014/0276923 A1 | 9/2014 | Miller |
| 2014/0277003 A1 | 9/2014 | Hendrick |
| 2014/0288525 A1 | 9/2014 | Fudaba et al. |
| 2014/0296889 A1 | 10/2014 | Avneri et al. |
| 2014/0309533 A1 | 10/2014 | Yamashita et al. |
| 2014/0330286 A1 | 11/2014 | Wallace |
| 2014/0343537 A1 | 11/2014 | Eversull et al. |
| 2014/0350645 A1 | 11/2014 | Diller et al. |
| 2014/0358123 A1 | 12/2014 | Ueda |
| 2014/0371718 A1 | 12/2014 | Alvarez et al. |
| 2015/0005704 A1 | 1/2015 | Heisel et al. |
| 2015/0046148 A1 | 2/2015 | Oh et al. |
| 2015/0105729 A1 | 4/2015 | Valeti et al. |
| 2015/0119859 A1 | 4/2015 | Cajamarca et al. |
| 2015/0126861 A1 | 5/2015 | Gambhir et al. |
| 2015/0133978 A1 | 5/2015 | Paul, Jr. |
| 2015/0157220 A1 | 6/2015 | Fish et al. |
| 2015/0157772 A1 | 6/2015 | Li et al. |
| 2015/0173782 A1 | 6/2015 | Garrison et al. |
| 2015/0174363 A1 | 6/2015 | Sutermeister et al. |
| 2015/0174368 A1 | 6/2015 | Garrison et al. |
| 2015/0257659 A1 | 9/2015 | Broers et al. |
| 2015/0290390 A1 | 10/2015 | Ring et al. |
| 2015/0335288 A1 | 11/2015 | Toth et al. |
| 2015/0335857 A1 | 11/2015 | Ishikawa |
| 2015/0359547 A1 | 12/2015 | Vale et al. |
| 2015/0366518 A1 | 12/2015 | Sampson |
| 2016/0000443 A1 | 1/2016 | Lilburn et al. |
| 2016/0008572 A1 | 1/2016 | Di Capriov |
| 2016/0030079 A1 | 2/2016 | Cohen |
| 2016/0038174 A1 | 2/2016 | Bruzzi et al. |
| 2016/0051386 A1 | 2/2016 | Haarmann-Theimann |
| 2016/0058459 A1 | 3/2016 | Bowman |
| 2016/0058513 A1 | 3/2016 | Giorgi |
| 2016/0081825 A1 | 3/2016 | Sudin et al. |
| 2016/0100819 A1 | 4/2016 | Tieu |
| 2016/0128688 A1 | 5/2016 | Garrison et al. |
| 2016/0129221 A1 | 5/2016 | Haverkost et al. |
| 2016/0135829 A1 | 5/2016 | Holochwost et al. |
| 2016/0144157 A1 | 5/2016 | Gulachenski et al. |
| 2016/0151010 A1 | 6/2016 | Erez |

(56) References Cited

U.S. PATENT DOCUMENTS

| | | |
|---|---|---|
| 2016/0166265 A1 | 6/2016 | Nita |
| 2016/0199204 A1 | 7/2016 | Pung et al. |
| 2016/0199620 A1 | 7/2016 | Pokorney et al. |
| 2016/0206216 A1 | 7/2016 | Kirenko |
| 2016/0206322 A1 | 7/2016 | Fitz et al. |
| 2016/0213396 A1 | 7/2016 | Dowell et al. |
| 2016/0220265 A1 | 8/2016 | Pokorney et al. |
| 2016/0220741 A1 | 8/2016 | Garrison et al. |
| 2016/0242764 A1 | 8/2016 | Garrison et al. |
| 2016/0242893 A1 | 8/2016 | Joshi et al. |
| 2016/0243157 A1 | 8/2016 | Cruise et al. |
| 2016/0256611 A1 | 9/2016 | Fitz |
| 2016/0271315 A1 | 9/2016 | Chang |
| 2016/0296690 A1 | 10/2016 | Kume et al. |
| 2016/0311990 A1 | 10/2016 | Cruise et al. |
| 2016/0317156 A1 | 11/2016 | Fitz et al. |
| 2016/0317173 A1 | 11/2016 | Hendrick |
| 2016/0317288 A1 | 11/2016 | Rogers et al. |
| 2016/0345904 A1 | 12/2016 | Bowman |
| 2016/0346508 A1 | 12/2016 | Williams et al. |
| 2016/0346515 A1 | 12/2016 | Buller |
| 2016/0354532 A1 | 12/2016 | Olesky et al. |
| 2016/0361180 A1 | 12/2016 | Vong et al. |
| 2016/0361459 A1 | 12/2016 | Baldwin |
| 2016/0367274 A1 | 12/2016 | Wallace |
| 2016/0367275 A1 | 12/2016 | Wallace |
| 2017/0007264 A1 | 1/2017 | Cruise et al. |
| 2017/0007277 A1 | 1/2017 | Drapeau et al. |
| 2017/0020540 A1 | 1/2017 | Chou et al. |
| 2017/0021172 A1 | 1/2017 | Perez et al. |
| 2017/0027604 A1 | 2/2017 | Wallace |
| 2017/0028170 A1 | 2/2017 | Ho |
| 2017/0035436 A1 | 2/2017 | Morita |
| 2017/0035446 A1 | 2/2017 | Rapaport et al. |
| 2017/0042548 A1 | 2/2017 | Lam |
| 2017/0043124 A1 | 2/2017 | Vreeman |
| 2017/0056061 A1 | 3/2017 | Ogle et al. |
| 2017/0072163 A1 | 3/2017 | Lim et al. |
| 2017/0072165 A1 | 3/2017 | Lim et al. |
| 2017/0072452 A1 | 3/2017 | Monetti et al. |
| 2017/0079680 A1 | 3/2017 | Bowman |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0087340 A1 | 3/2017 | Peralta et al. |
| 2017/0100126 A1 | 4/2017 | Bowman et al. |
| 2017/0100142 A1 | 4/2017 | Look et al. |
| 2017/0105743 A1 | 4/2017 | Vale et al. |
| 2017/0143938 A1 | 5/2017 | Ogle et al. |
| 2017/0147765 A1 | 5/2017 | Mehta |
| 2017/0164964 A1 | 6/2017 | Galdonik et al. |
| 2017/0172581 A1 | 6/2017 | Bose et al. |
| 2017/0172766 A1 | 6/2017 | Vong et al. |
| 2017/0181835 A1 | 6/2017 | Kleshinski et al. |
| 2017/0189033 A1 | 7/2017 | Sepetka et al. |
| 2017/0209260 A1 | 7/2017 | Garrison et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224953 A1 | 8/2017 | Tran et al. |
| 2017/0246014 A1 | 8/2017 | Rapaport et al. |
| 2017/0252057 A1 | 9/2017 | Bonnette et al. |
| 2017/0259037 A1 | 9/2017 | Kern et al. |
| 2017/0265869 A1 | 9/2017 | Cibulski et al. |
| 2017/0265983 A1 | 9/2017 | Lam et al. |
| 2017/0274180 A1 | 9/2017 | Garrison et al. |
| 2017/0281192 A1 | 10/2017 | Tieu et al. |
| 2017/0281204 A1 | 10/2017 | Garrison et al. |
| 2017/0283536 A1 | 10/2017 | Cruise et al. |
| 2017/0303949 A1 | 10/2017 | Jacobi et al. |
| 2017/0340867 A1 | 11/2017 | Accisano |
| 2017/0348514 A1 | 12/2017 | Guyon et al. |
| 2017/0354421 A1 | 12/2017 | Maguire et al. |
| 2017/0354523 A1 | 12/2017 | Chou et al. |
| 2017/0354803 A1 | 12/2017 | Kume et al. |
| 2017/0360450 A1 | 12/2017 | Tompkins et al. |
| 2017/0361072 A1 | 12/2017 | Chou et al. |
| 2017/0367713 A1 | 12/2017 | Green et al. |
| 2017/0367857 A1 | 12/2017 | Bennett et al. |
| 2017/0368296 A1 | 12/2017 | Chang |
| 2017/0368309 A1 | 12/2017 | Garrison et al. |
| 2018/0008294 A1 | 1/2018 | Garrison et al. |
| 2018/0008439 A9 | 1/2018 | Tieu et al. |
| 2018/0014840 A1 | 1/2018 | Paniam |
| 2018/0028205 A1 | 2/2018 | Chou et al. |
| 2018/0028209 A1 | 2/2018 | Sudin et al. |
| 2018/0036155 A1 | 2/2018 | Tieu et al. |
| 2018/0042623 A1 | 2/2018 | Batiste |
| 2018/0055364 A1 | 3/2018 | Pierro |
| 2018/0055516 A1 | 3/2018 | Bagaoisan et al. |
| 2018/0104390 A1 | 4/2018 | Kilcran |
| 2018/0169508 A1 | 6/2018 | Billardello et al. |
| 2018/0200478 A1 | 7/2018 | Lorenzo et al. |
| 2018/0207395 A1 | 7/2018 | Bulman et al. |
| 2018/0207399 A1 | 7/2018 | Chou et al. |
| 2018/0228502 A1 | 8/2018 | Shaffer et al. |
| 2018/0242962 A1 | 8/2018 | Walen et al. |
| 2018/0242980 A1 | 8/2018 | Lubock et al. |
| 2018/0242989 A1 | 8/2018 | Nita |
| 2018/0242999 A1 | 8/2018 | Thatipelli |
| 2018/0250013 A1 | 9/2018 | Wallace et al. |
| 2018/0263632 A1 | 9/2018 | Seifert et al. |
| 2018/0263642 A1 | 9/2018 | Nita |
| 2018/0279965 A1 | 10/2018 | Pandit et al. |
| 2018/0289340 A1 | 10/2018 | Trindade Rodrigues et al. |
| 2018/0296236 A1 | 10/2018 | Goldfarb et al. |
| 2018/0307362 A1 | 10/2018 | Komala et al. |
| 2018/0338770 A1 | 11/2018 | Mogi et al. |
| 2018/0353194 A1 | 12/2018 | Shaffer et al. |
| 2019/0022363 A1 | 1/2019 | Grayzel et al. |
| 2019/0029825 A1 | 1/2019 | Fitterer et al. |
| 2019/0030305 A1 | 1/2019 | Aboytes |
| 2019/0070387 A1 | 3/2019 | Goyal |
| 2019/0105477 A1 | 4/2019 | Heilman et al. |
| 2019/0105478 A1 | 4/2019 | Malek et al. |
| 2019/0108540 A1 | 4/2019 | Look et al. |
| 2019/0125393 A1 | 5/2019 | Hendrick |
| 2019/0167124 A1 | 6/2019 | Verkruijsse et al. |
| 2019/0175030 A1 | 6/2019 | Verkruijsse et al. |
| 2019/0200871 A1 | 7/2019 | De Haan |
| 2019/0239910 A1 | 8/2019 | Brade et al. |
| 2019/0275290 A1 | 9/2019 | Yamashita et al. |
| 2019/0290884 A1 | 9/2019 | Kanemasa et al. |
| 2019/0329003 A1 | 10/2019 | Watanabe |
| 2019/0336142 A1 | 11/2019 | Torrie |
| 2019/0351182 A1 | 11/2019 | Chou et al. |
| 2020/0008820 A1 | 1/2020 | Aboytes et al. |
| 2020/0009350 A1 | 1/2020 | Goyal |
| 2020/0022712 A1 | 1/2020 | Deville et al. |
| 2020/0023160 A1 | 1/2020 | Chou et al. |
| 2020/0046368 A1 | 2/2020 | Merritt et al. |
| 2020/0046937 A1 | 2/2020 | Nakagawa et al. |
| 2020/0170521 A1 | 6/2020 | Gupta et al. |
| 2020/0171276 A1 | 6/2020 | Onozuka |
| 2020/0171277 A1 | 6/2020 | Garrison et al. |
| 2020/0187979 A1 | 6/2020 | Bowman |
| 2020/0188630 A1 | 6/2020 | Fujita et al. |
| 2020/0205845 A1 | 7/2020 | Yang et al. |
| 2020/0276411 A1 | 9/2020 | Ogle et al. |
| 2020/0289136 A1 | 9/2020 | Chou |
| 2020/0297972 A1 | 9/2020 | Yee et al. |
| 2020/0306501 A1 | 10/2020 | Yee et al. |
| 2020/0337716 A1 | 10/2020 | Garrison et al. |
| 2020/0345979 A1 | 11/2020 | Loh et al. |
| 2021/0001141 A1 | 1/2021 | Pfiffner et al. |
| 2021/0045758 A1 | 2/2021 | Garrison et al. |
| 2021/0052296 A1 | 2/2021 | Garrison |
| 2021/0068852 A1 | 3/2021 | Spence |
| 2021/0093336 A1 | 4/2021 | Roue |
| 2021/0106792 A1 | 4/2021 | Rafiee |
| 2021/0128182 A1 | 5/2021 | Teigen et al. |
| 2021/0146094 A1 | 5/2021 | Christian et al. |

(56) References Cited

U.S. PATENT DOCUMENTS

| | | |
|---|---|---|
| 2021/0153744 A1 | 5/2021 | Pierro |
| 2021/0186537 A1 | 6/2021 | Buck et al. |
| 2021/0187244 A1 | 6/2021 | Buck et al. |
| 2021/0307767 A1 | 10/2021 | Gifford, III et al. |
| 2021/0315598 A1 | 10/2021 | Buck et al. |
| 2021/0316127 A1 | 10/2021 | Buck et al. |
| 2021/0361909 A1 | 11/2021 | Cottone et al. |
| 2021/0378527 A1 | 12/2021 | Strasser et al. |
| 2021/0378696 A1 | 12/2021 | Yang et al. |
| 2021/0393275 A1 | 12/2021 | Whelan |
| 2021/0393276 A1 | 12/2021 | Whelan |
| 2022/0047849 A1 | 2/2022 | Yee et al. |
| 2022/0080158 A1 | 3/2022 | McLaughlin et al. |
| 2022/0151646 A1 | 5/2022 | Dholakia et al. |
| 2022/0168010 A1 | 6/2022 | Brinkmann et al. |
| 2022/0211975 A1 | 7/2022 | Yang et al. |
| 2022/0287785 A1 | 9/2022 | Hassan et al. |
| 2022/0330960 A1 | 10/2022 | Buck et al. |
| 2022/0331085 A1 | 10/2022 | Buck et al. |
| 2022/0331509 A1 | 10/2022 | Buck et al. |

FOREIGN PATENT DOCUMENTS

| | | |
|---|---|---|
| CN | 101321552 A | 12/2008 |
| CN | 101340849 A | 1/2009 |
| CN | 101795631 A | 8/2010 |
| CN | 201596219 U | 10/2010 |
| CN | 102319097 A | 1/2012 |
| CN | 102573701 A | 7/2012 |
| CN | 102844071 A | 12/2012 |
| CN | 102847220 A | 1/2013 |
| CN | 103648574 A | 3/2014 |
| CN | 103764214 A | 4/2014 |
| CN | 204158457 U | 2/2015 |
| CN | 104548316 A | 4/2015 |
| CN | 104622538 A | 5/2015 |
| CN | 105120776 A | 12/2015 |
| CN | 105208951 A | 12/2015 |
| CN | 204909516 U | 12/2015 |
| CN | 107405159 A | 11/2017 |
| CN | 110916768 | 3/2020 |
| DE | 8900059 | 5/1989 |
| DE | 10 2010 053111 | 6/2012 |
| DE | 10 2012 112732 | 6/2014 |
| EP | 0 330 843 | 12/1993 |
| EP | 0 582 533 | 2/1994 |
| EP | 0 309 471 | 8/1996 |
| EP | 1 349 486 | 3/2008 |
| EP | 2 069 528 | 3/2013 |
| EP | 2 937 108 | 10/2015 |
| EP | 2 928 360 | 1/2017 |
| EP | 2 211 732 | 5/2018 |
| EP | 3 539 486 | 9/2019 |
| EP | 3 698 740 | 8/2020 |
| GB | 2077132 | 12/1981 |
| JP | 2002-535049 | 10/2002 |
| JP | 2003-527925 | 9/2003 |
| JP | 2006-102222 | 4/2006 |
| JP | 2006-521881 | 9/2006 |
| JP | 2008-502378 | 1/2008 |
| JP | 2013-504388 | 2/2013 |
| JP | 2014-515670 | 7/2014 |
| JP | 2015-504327 | 2/2015 |
| WO | WO 1995/009659 | 4/1995 |
| WO | WO 2000/000100 | 1/2000 |
| WO | WO 2006/101170 | 9/2006 |
| WO | WO 2009/054968 | 4/2009 |
| WO | WO 2009/132218 | 10/2009 |
| WO | WO 2010/126786 | 11/2010 |
| WO | WO 2014/151209 | 9/2014 |
| WO | WO 2014/203336 | 12/2014 |
| WO | WO 2016/001712 | 1/2016 |
| WO | WO 2017/025775 | 2/2017 |
| WO | WO 2018/121363 | 7/2018 |
| WO | WO 2019/178165 | 9/2019 |
| WO | WO 2019/222518 | 11/2019 |
| WO | WO 2019/246583 | 12/2019 |
| WO | WO 2020/145928 | 7/2020 |
| WO | WO 20/263630 | 12/2020 |
| WO | WO 2021/016213 | 1/2021 |
| WO | WO 2021/064955 | 4/2021 |
| WO | WO 2021/090821 | 5/2021 |
| WO | WO 2021/105658 | 6/2021 |
| WO | WO 2021/242734 | 12/2021 |

OTHER PUBLICATIONS

Bernava et al., Sep. 23, 2019, Direct trhomboaspiration efficacy for mechanical thrombectomy is related to the angle of interaction between the catheter and the clot, J. NeuroIntervent Surg., 0:1-6, doi:10.1136/neurintsurg-2019-015113.

GUIDEZILLA Guide Extension Catheter, Boston Scientific 510k Submission, Feb. 20, 2017.

Korpelainen et al., 1995, Asymmetrical skin temperature in ischemic stroke, Stroke, 26(9):1543-1547.

Merit Medical Systems Acquired Distal Access's SPINR Platform, Jul. 15, 2015, Digital Access, LLC; Merit Medical Systems, 5 pages.

Simon et al., *Exploring the efficacy of cyclic vs. static aspiration in a cerebral thrombectomy model: an initial proof of concept study*, J. NeuroIntervent Surg 2014, 6 pp. 677-683.

Simon et al., *Hydrodynamic comparison of the Penumbra system and commonly available syringes in forced—suction thrombectomy*, J. NeuroIntervent Surg 2014, 6, pp. 205-211.

Spiotta et al., Evolution of thrombectomy approaches and devices for acute stroke: a technical review, J. NeuroIntervent Surg 2015, 7, pp. 2-7.

Invitation to Pay Additional Fees for International Application No. PCT/US20/65349 dated Feb. 24, 2021.

International Search Report and Written Opinion dated May 7, 2021 in application No. PCT/US20/65349.

* cited by examiner

MANUALLY ROTATABLE THROMBUS ENGAGEMENT TOOL

INCORPORATION BY REFERENCE

This application claims the priority benefit under 35 U.S.C. § 119(e) of U.S. Provisional Patent Application No. 63/341,926, filed May 13, 2022, and is a continuation-in-part of U.S. patent application Ser. No. 17/357,490, filed Jun. 24, 2021, which claims the priority benefit under 35 U.S.C. § 119(e) of U.S. Provisional Patent Application No. 63/044,511, filed Jun. 26, 2020, and which is a continuation-in-part of U.S. patent application Ser. No. 17/125,723, filed Dec. 17, 2020, and issued as U.S. Pat. No. 11,065,018 on Jul. 20, 2021, which claims the priority benefit under 35 U.S.C. § 119(e) of U.S. Provisional Patent Application No. 62/950,058, filed Dec. 18, 2019, and U.S. Provisional Patent Application No. 63/064,273, filed Aug. 11, 2020, the entireties of each of which are hereby incorporated by reference herein.

BACKGROUND

Removal of blood clots from the vascular system (thrombectomy) using a trans vascular approach may be accomplished at any of a variety of treatment sites, such as arteries in the extremities, veins for deep vein thrombosis (DVT), large veins and arteries (central vessels) such as iliac veins and arteries, the aorta, the inferior vena cava and pulmonary arteries to treat pulmonary emboli (PE).

For example, venous thromboembolic disease (VTE) is a worldwide crisis. There are over 10 million cases of DVT and PE diagnosed globally per year, with 1 million cases occurring in the United States and over 700,000 in France, Italy, Germany, Spain, Sweden, and the United Kingdom combined each year. There are approximately 60,000 to 100,000 deaths from PE in the United States each year. DVT and PE are part of the same continuum of disease, with over 95% of emboli originating in the lower extremities. When PE occurs, the severity depends on the embolic burden and its effect on the right ventricle as well as underlying cardio-pulmonary comorbidities. Death can result from the acute increase in pulmonary artery (PA) pressure with increased right ventricular (RV) afterload and dysfunction.

Patients with high-risk PE have been treated primarily with thrombolytic therapy delivered systemically or more locally through Catheter Directed Thrombolytics. These approaches result in multiple catheterization lab visits, lengthy hospital stays and often lead to bleeding complications. Newer approaches to PE treatment include single session thrombectomy treatments without the use of thrombolytics. These thrombectomy treatments include delivering a catheter into the PA to remove the thrombus through aspiration, and secondary tools may also macerate or disrupt the thrombus prior to aspiration. While thrombectomy results in fewer bleeding complications and reduced hospital stays compared to thrombolytics, there is much to be improved upon given the challenges of the procedure itself, including the ability to capture a broad spectrum of thrombus types and reduce the total volume of blood loss during the procedure.

The thrombectomy catheter is introduced through an introducer puncture in a large diameter vein. A flexible guide wire is passed through the introducer into the vein and the introducer is removed. The flexible guidewire provides a rail for a flexible guide catheter to be advanced through the right atrium into the right ventricle and into the pulmonary artery. The flexible guidewire is removed and replaced with a stiff guidewire. The large diameter thrombectomy catheter with support dilator is then advanced over the stiff guidewire to the pulmonary artery and the dilator is removed. If the large diameter thrombectomy catheter is not successful in accessing or aspirating thrombus in a more distal portion of the vessel, a smaller diameter catheter may be inserted through the large diameter catheter.

In addition, peripheral arterial occlusive (PAO) disease occurs in more than 4% of individuals over age 40 and markedly increases in incidence after the age of 70. Acute PAO is usually due to thrombosis of the peripheral vasculature and is associated with a significant risk of limb loss. In order to preserve the limb, therapy for acute PAO centers on the rapid restoration of arterial patency and blood flow such as through mechanical thrombectomy in procedures similar to those described above.

Clot aspiration using certain commercial vacuum-assisted thrombectomy systems may sometimes need to be terminated due to the risk of excessive blood loss by the patient, especially when using large aspiration catheters. During aspiration thrombectomy, when the catheter tip falls out of contact with the thrombus or other occlusive material, the tip is exposed to healthy blood and full flow of blood through the catheter ensues. Under such conditions, the total volume of blood loss may be excessive, and in some cases, may result in premature termination of the procedure. For example, during a procedure when the catheter enters healthy blood and full aspiration flow ensues, the blood loss rate can be on the order of 30-40 cc per second with an 24 French size catheter. With a maximum tolerable blood loss on the order of about 500 mL, the catheter cannot run in unrestricted mode for more than approximately 10 to 15 seconds. The aggregate blood loss may reach an unacceptable level before sufficient clot is removed.

Thus, notwithstanding prior efforts, there remains a need for an improved technology for removing or reducing thrombotic restrictions and occlusions within either the patient's arterial or venous blood vessels.

SUMMARY

There is provided in accordance with one aspect of the present invention, a clot capture module for use in a thrombectomy system, such as within the sterile field. The clot capture module comprises a housing; a clot capture chamber in the housing; a window in the housing to permit visual inspection of the clot chamber; and a filter in the clot chamber, visible through the window, the filter having an upstream surface and a downstream surface.

An incoming flow path is configured to direct incoming blood from an aspiration catheter against the upstream surface of the filter. An aspiration control valve is provided in the incoming flow path, configured to block or permit the flow of incoming blood. An outgoing flow path is configured to direct blood from the second side of the filter to a remote vacuum canister.

The clot capture module may further comprise a vent valve, openable to permit an optically transparent media such as air or saline to be drawn into the clot chamber, enabling blood to be evacuated from the clot chamber to a remote canister. The upstream surface of the filter may be visible through the window, so that clot accumulated on the upstream surface can be visually observed through the window, once the vent has been opened to evacuate blood from the clot capture chamber. The window may comprise a transparent cylindrical portion of the housing.

The upstream surface of the filter may be substantially planar. Alternatively, the upstream surface of the filter may be convex. The filter may comprise a tubular porous membrane such as a cylinder, and the upstream surface of the filter may be on a radially outwardly facing surface of the membrane. The tubular filter membrane may enclose a filtered blood chamber which is in communication with the outgoing flow path.

The module may further comprise an aspiration control, for controlling the aspiration control valve. The aspiration control may comprise a rocker switch, configured to selectively collapse or allow reopening of a collapsible tubing. The aspiration control valve may be normally closed, and may be spring biased into the closed configuration.

The clot capture module may be provided in combination with a vacuum line leading to an aspiration pump and canister, wherein the clot capture module is configured to reside within a sterile field and the aspiration pump and canister are outside of the sterile field. The vacuum line may be at least about 30 inches or 50 inches or more in length. In some instances, a manually actuated aspiration device (e.g., a syringe) may be used in addition to, or as an alternative to, an aspiration pump to permit a user to manually apply aspiration through the vacuum line.

There is provided in accordance with another aspect of the present invention, a thrombus engagement tool, configured to advance through an aspiration catheter and engage thrombus. The thrombus engagement tool comprises a rotatable core wire having a proximal end and a distal end; and a thrombus engagement tip on the distal end of the core wire. The tip may comprise a helical thread; an advance segment on a distal side of the thread and a trailing segment on a proximal side of the thread. The advance segment, helical thread and trailing segment may all be molded onto the core wire.

The thrombus engagement tool may further comprise a projection on the core wire, underneath at least one of the advance segment and the trailing segment, to form an interference fit with the thrombus engagement tip. The projection may comprise an annular ring, which may be a radiopaque marker. The thrombus engagement tool may comprise a first radiopaque marker under the advance segment and a second radiopaque marker under the trailing segment.

An outer periphery of the helical thread may substantially conform to an inside surface of a cylinder. The thread may comprise a proximal surface which inclines radially outwardly in a proximal direction to define a proximally opening undercut.

The thrombus engagement tool may further comprise a handle on the proximal end of the core wire configured for hand turning the core wire. A limit bearing surface may be provided on the handle, for limiting distal projection of the thrombus engagement tip relative to a distal end of the aspiration catheter.

There is further provided a method of removing embolic material from a vessel with mechanical and aspiration assistance. The method comprises the steps of providing an aspiration catheter having a central lumen and a distal end; advancing the distal end to obstructive material in a vessel; applying vacuum to the lumen to draw clot at least partially into the lumen; and introducing a thrombus engagement tool into the lumen. The thrombus engagement tool may have a tip with an axial length of no more than about 1 cm or about 5 mm and a helical thread having a major diameter that is at least about 0.015 inches smaller than an inside diameter of the lumen, to provide an aspiration flow path through the lumen around the outside of the tip. The method further comprises manually rotating the tip to engage clot between the tip and an inside wall of the lumen.

A method of aspirating a vascular occlusion from a remote site, comprises the steps of advancing an elongate tubular body through a vascular access site and up to a vascular occlusion, the tubular body comprising a proximal end, a distal end, a central lumen, and a stop surface. A rotatable core is advanced distally through the lumen until a limit surface carried by the core rotatably slidably engages the stop surface to provide a rotatable bearing which limits further distal advance of the core within the lumen. Vacuum is applied to the lumen and the core is manually rotated to engage thrombus. The advancing the rotatable core may be accomplished after the step of advancing the elongate tubular body through the vascular access site and up to the vascular occlusion. The core may be a solid core wire or a cannulated structure such as a hypotube or microcatheter having a central lumen extending axially between a proximal opening and a distal opening.

The core may carry a proximal handle, and the limit surface may be carried by the handle. The tubular body may include a proximal hub, and the stop surface may be carried by the hub. The core may carry an engagement tip having a helical thread, and the engaging thrombus step may comprise pinning thrombus between a first side of the tip and an inside surface of the tubular body.

There is also provided an inserter for guiding a device through a hemostasis valve, comprising an elongate tubular body, having a proximal end, a distal end and a central lumen; a laterally facing concave landing zone on the proximal end, having a radius of curvature that increases in the proximal direction; and an axially extending slit in the sidewall, extending from the distal end to the landing zone. The tubular body may further comprise a tapered distal tip, and a proximal pull tab to facilitate removal of the inserter from the device. A surface of the landing zone may comprises a different color than an outside surface of the tubular body, to facilitate visualization of the landing zone and advancing the distal end of the device into the tubular body.

A method of passing a device through a hemostasis valve may comprise the steps of providing an inserter, having a tubular body with a split sidewall; advancing the tubular body through a hemostasis valve; advancing a device through the tubular body and beyond the hemostasis valve; and proximally retracting the tubular body so that the device escapes laterally from the tubular body through the split sidewall, leaving the device in place across the hemostasis valve.

The advancing the tubular body step may comprise advancing a tapered distal tip on the tubular body through the hemostasis valve. The advancing the tubular body through the hemostasis valve step may be accomplished with the device pre loaded inside the tubular body.

A distal nose segment of the tubular body may expand in diameter in response to advancing the device therethrough. The device may be a thrombus engagement tool or a secondary catheter. The secondary catheter may be an aspiration catheter.

DETAILED DESCRIPTION

Figure 1:
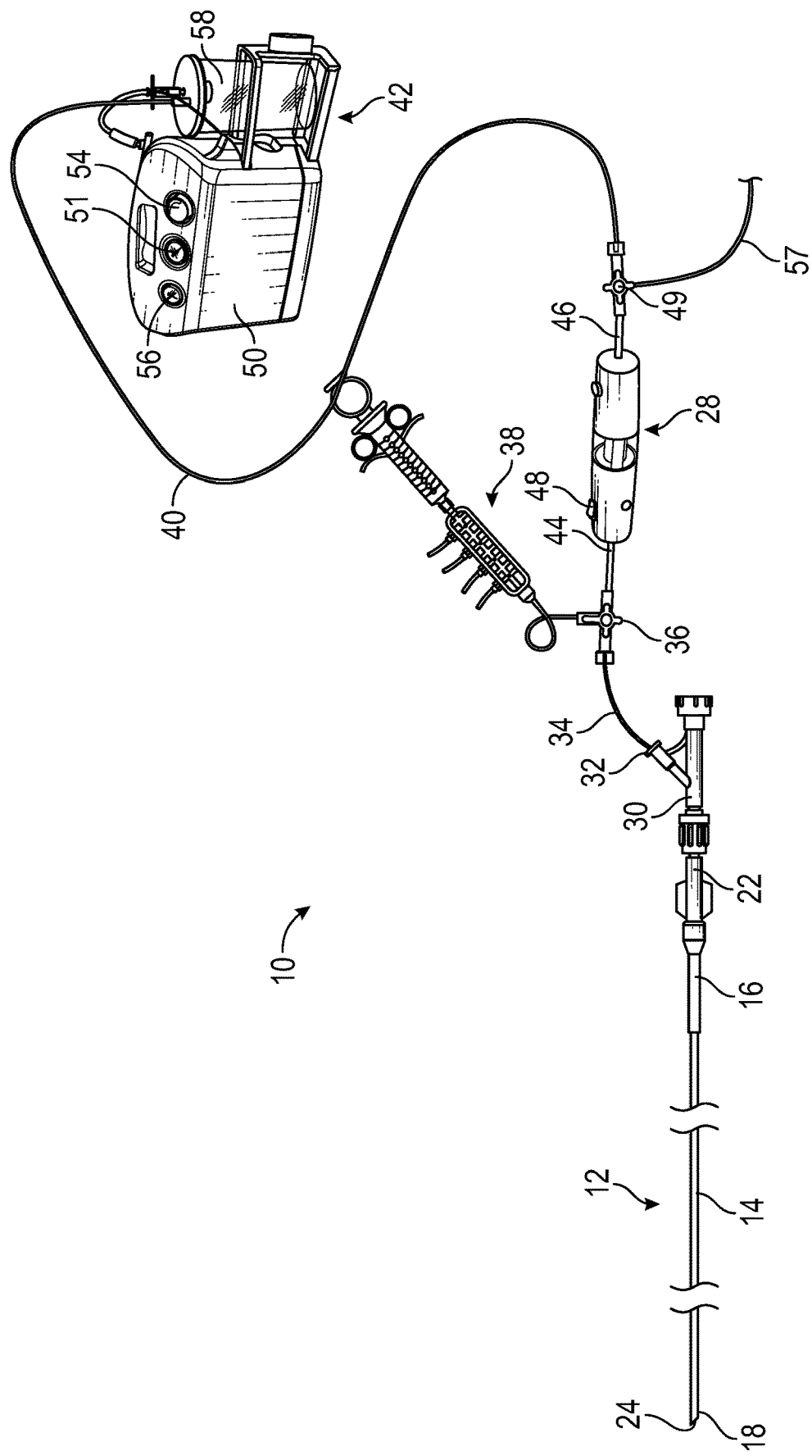
FIG. 1 is a schematic view of a thrombus removal system in accordance with the present invention.

Referring to FIG. 1, there is illustrated a thrombectomy system such as for PE or DVT aspiration procedures. The system 10 includes a thrombectomy catheter 12, having an elongate tubular body 14 extending between the proximal end 16 and a distal end 18. A central lumen 20 (not illustrated in FIG. 1) extends between a proximal catheter connector 22 and a distal port 24 on the distal end 18.

Although primarily described in the context of an aspiration catheter with a single central lumen, catheters of the present invention can readily be modified to incorporate additional structures, such as permanent or removable column strength enhancing mandrels, two or more lumen such as to permit drug, contrast or irrigant infusion or to supply inflation media to an inflatable balloon carried by the catheter, or any combinations of these features, as will be readily apparent to one of skill in the art in view of the disclosure herein. In addition, the disclosure will be described primarily in the context of removing obstructive material from the vasculature, but it will be understood to have applicability as an access catheter for delivery and removal of any of a variety of diagnostics or therapeutic devices with or without aspiration.

The catheters disclosed herein may readily be adapted for use throughout the body wherever it may be desirable to distally advance a low profile high flexibility catheter into a variety of type of vasculature, such as small or large vasculature and/or tortuous or relatively straight vasculature. For example, catheter shafts in accordance with any embodiment described herein may be dimensioned for use throughout the neurovascular, coronary and peripheral vasculature, the gastrointestinal tract, the urethra, ureters, Fallopian tubes and other lumens and potential lumens, as well. The catheter shaft construction of any embodiment herein may also be used to provide minimally invasive percutaneous tissue access, such as for diagnostic or therapeutic access to a solid tissue target (e.g., breast or liver or brain biopsy or tissue excision), delivery of laparoscopic tools or access to bones such as the spine for delivery of screws, bone cement or other tools or implants.

Catheter 12 will have a length and diameter suitable for the intended access point and target location. In one example, referring to FIG. 1, the catheter 12 may have an effective length from the distal end of manifold or hub 22 to distal tip 18 generally no more than about 230 cm, no more than about 210 cm, no more than about 180 cm, or no more than about 160 cm. and typically from about 50 cm to about 150 cm, from about 90 cm to about 130 cm, or from about 105 cm to about 115 cm. The outer diameter of the catheter 10 may be from about 0.035 inches to about 0.15 inches, from about 0.09 inches to about 0.13 inches, and may be lower in a distal segment than in a proximal segment.

The inner diameter of the catheter 12 in a single central lumen embodiment may be greater than or equal to about 0.1 inches, greater than or equal to about 0.088 inches, or greater than or equal to about 0.08 inches, or greater than or equal to about 0.06. The inner diameter of the catheter 12 in a single central lumen embodiment may be less than about 0.20 inches or 0.15 inches, or less than or equal to about 0.11 inches, less than or equal to about 0.1 inches, less than or equal to about 0.088 inches, or less than or equal to about 0.07 inches, and often no more than about 0.095 inches.

In the illustrated embodiment, the catheter 12 is releasably connectable to a flow control module 28 by way of a complementary connector module 30. Connector module 30 provides a releasable connection to complementary catheter connector 22 and may include a side port 32 for releasable connection to tubing 34 which may lead to a valve 36. Connector module 30 may additionally comprise a hemostasis valve configured to receive another device such as a guidewire or thrombus engagement tool, discussed below.

Valve 36 may selectively place tubing 34 into communication with side port 37 or the flow control module 28 discussed in greater detail below. Side port 37 may be placed into communication with a source of media such as saline, contrast solution or medication, or a manifold 38 which can provide selective communication with each. The use of valve 36 allows infusion of a desired media without detaching the tubing 34 from the connector module 30.

Figure 2:
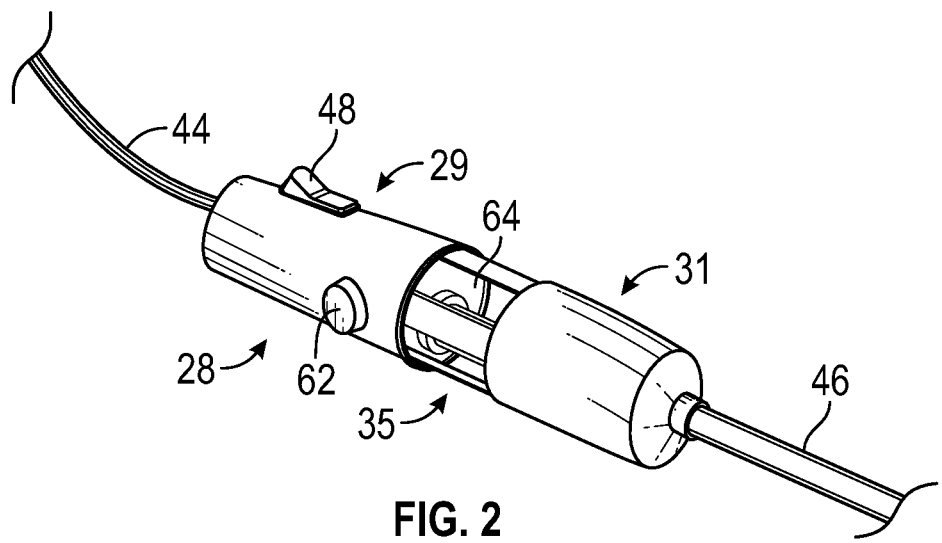
FIG. 2 is a perspective view of a flow control module.
Figure 3:
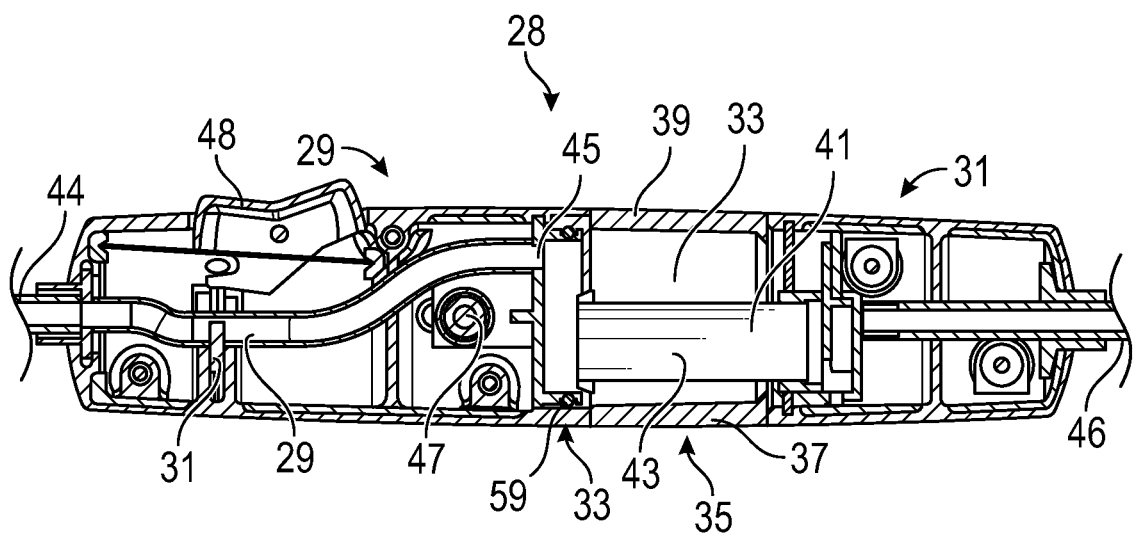
FIG. 3 is an elevational of cross-sectional view through the flow control module of FIG. 2.

Referring to FIGS. 2 and 3, the flow control module 28 is in communication with the valve 36 by way of a distal tube 44. Flow control module 28 is in communication with the selector valve 49 by way of a proximal tube 46. This establishes a flow path between the distal port 24 through the catheter 12 through the various tubing and flow control module 28 to the pump assembly 42. In an alternate implementation of the invention, the flow control module 28 may be integrally formed within the hub of thrombectomy catheter 12 to which the catheter 12 may be removably or non-removably attached or within the connector module 30. In some instances, a manually actuated aspiration device (e.g., a syringe) may be used in addition to, or as an alternative to, an aspiration pump assembly 42 to permit a user to manually apply aspiration through the vacuum line. It will be understood by one having skill in the art that a manually actuated aspiration device may be in in addition to, or as an alternative to, the pump assembly described in any embodiment herein.

Flow control module 28 may include a flow regulator such as an on-off control for regulating flow through the flow path between the catheter 12 and pump 42. The flow regulator is configured to provide a reversible restriction in the flow path, such as by an expandable or contractible iris, a ball valve or other rotary core valve, leaf valve, a pinch tubing, or others known in the art.

In one implementation, the flow regulator comprises a collapsible portion 29 of the tubular wall defining the flow path, such as a section of polymeric tubing. An actuator 31 positioned adjacent the tubing is movable in response to a control such as a push button or toggle switch 48 between a first position where it compresses the tubing, thereby completely restricting flow, and a second position where it has moved away from the tubing, allowing the tubing to resume its full inside diameter and allow fluid flow. The actuator 31 may be spring biased or have another default driver in the direction of the first (restricted) position, and only movable into the second (open) position in the presence of an affirmative mechanical force or release of a constraint allowing the flow path to open. Upon removal of the momentary "on" command, the actuator 31 automatically resumes the first position, obstructing flow.

The actuator 31 may be driven by a mechanical control such as a lever or rotatable knob, or an electrically driven system such as a solenoid, operated by any of a variety of buttons, levers, triggers, foot pedals or other switches known in the art, depending upon the desired functionality.

The flow control module 28 may contain a filter chamber 33 for example, which is in communication with the vacuum canister 58 on the pump assembly 42 by way of elongate aspiration tubing 40. The toggle switch 48 is in between the filter chamber 33 and the catheter 12. In a default off position of some embodiments, this allows the entire length of the aspiration tubing 40 and the filter chamber 33 to reach the same low pressure as the aspiration canister 58 on the pump 42.

Additional details of the filter assembly and related structures are illustrated in FIG. 3. A filter assembly 35 includes an outer tubular sidewall 37 having a transparent window 39. In some implementations the entire tubular sidewall 37 can be a transparent window. The side wall 37 encloses a filter 41. The filter 41 includes a filter sidewall 43 defining an interior (downstream) chamber (not illustrated) for filtered blood.

Upon opening the flow path by activating the switch 48, blood and thrombus are drawn in the direction from catheter 12 via vacuum line 44 through a first filter aperture 45 and into the clot collection chamber 33. Any thrombus will be captured on the outside (upstream side) of filter 43. Blood is drawn through the filter 43 and proximal tubing 46 en route to the canister 58. In the illustrated example, the filter 43 is tubular however it may alternatively be planar or other shape depending upon the desired configuration.

The switch 48 may thereafter be closed to compress tubing 29 and isolate the catheter 12 from the vacuum source. A normally closed vent 47 may be momentarily opened, to permit intake of an optically transparent media such as saline or ambient air. This allows residual blood in the chamber 33 to be drawn through the filter 43 and aspirated out via proximal tubing 46, enabling visualization of any clot on the surface of the filter 43 through the window 39. The vent 47 may be manually actuated by a user and/or automatically actuated by the system. In some instances, a user may manually actuate the vent 47 through actuation of a button 62 located on the flow control module 28.

For example, the vent 67 may be normally closed, and then transitioned to an open configuration when the button 62 is being actuated (or vice versa). When in the open configuration, the vent 67 may expose the clot collection chamber 33 to an ambient environment. In some instances, exposure of the chamber 33 to the ambient environment allowing intake of air and acceleration of blood flow through the clot collection chamber 33 and towards the proximal tubing. Increased acceleration of blood flow due to vent 47 actuation may facilitate visualization of the clot by displacing the amount of blood or other fluids from the optical path between the window and the filter and/or decrease the amount of time required for the physician to accurately identify the clot in the chamber 33. The valved vent also allows the physician to deliver pulsatile negative pressure waves at the distal opening 24.

In the illustrated embodiment, the flow control module 28 comprises a proximal housing 31 and a distal housing 29 separated by the transparent tubular sidewall 35. The tubular sidewall 35 and the filter 43 are carried by the proximal housing 31. Housing 29 and tubular sidewall 35 may be joined at a releasable connection 33 that, in some instances, includes a gasket 59 to form a sealed connection. Complementary surface structures (e.g., inclined corresponding grooves and pins or flanges) may permit rapid attachment and detachment. For example, the proximal housing 31 and the distal housing 29 may be rotated relative to each other (e.g., by relative rotation across the gasket) to disconnect the housings from each other.

The filter 43 may be attached to any one of the distal housing 29 or the proximal housing 31 upon disconnection of the housings. The tubular sidewall 35 may be attached to either one of the distal housing 29 and/or the proximal housing 31 such that, upon disconnection, the tubular sidewall 35 may remain attached to one of the housings 29, 31. Upon detaching and separating the proximal housing 31 from the distal housing 29, the tubular sidewall 35 may be configured to remain around the filter 43 or may be configured to be removed from over the filter 43. In either instance, disconnection of the housings 29, 31 from each other can expose the filter 43 and allow a clot to be easily accessed and removed.

The interior surface of the clot collection container 33 may comprise a coating to provide one or more of a variety of properties to the clot collection containers 33. In some instances, the coating may be configured to enhance visualization through at least a portion of the clot collection container 33 (such as the transparent window 39). The coating may be configured to inhibit blood accumulation or increase blood repellant properties. In some instances, the clot collection container 33 may comprise a coating to inhibit foam formation during an aspiration procedure. The coatings may be located at least partially along an interior surface of the tubular sidewall 35 and/or the clot collection container 33 or along an entire interior surface of the tubular sidewall 35 and/or the clot collection container 33. In some instance, the coating is located along an interior surface of the transparent window 39. The coating can be both hydrophobic and oleophobic. In some instances, the coating may have some hydrophilic features on a portion of the polymer to increase oleophobic properties.

Aspiration pump assembly 42 may be releasably placed into communication with flow control module 28 such as by a luer connection between selector valve 45 and tubing 40. Aspiration pump assembly 42 may include a vacuum pump 50, and may also include a vacuum gauge 51, and an optional pressure adjustment control 54. The vacuum gauge 51 is in fluid communication with the vacuum pump and indicates the vacuum pressure generated by the pump. The pressure adjustment control 54 allows the user to set to a specific vacuum pressure. Power button 56 activates the pump 50.

The vacuum canister 58 may be provided with a vent 53 to atmosphere, opened or closed by a valve. In one implementation the valve is normally closed to permit vacuum in the canister to reach a desired low pressure. The valve may be momentarily opened as desired to permit introduction of air and reduction of the vacuum, such as to reduce foaming within the vacuum canister 58.

The vent may function to reduce foaming and increase visibility within the canister. In some instances, the vent 53 comprises a permanently opened vent such as in a lid or side wall of the vacuum canister. The vent may comprise an aperture formed through the lid or side wall having a diameter of no more than about 0.5 mm or 0.25 mm and may be a laser cut hole through a metal sheet which may be in the form of a disc carried by the lid.

In addition to or as an alternative to the vent, the inside surface of the canister 58 may be provided with a coating of one or more materials to inhibit foaming of blood under vacuum. The coatings may be located at least partially along or entirely along an interior surface of the vacuum canister 58. The coating can be both hydrophobic and oleophobic. In some instances, the coating may have some hydrophilic features on a portion of the polymer to increase oleophobic properties.

Any of a variety of controls may be utilized to operate the various pump functions, including switches, buttons, levers, rotatable knobs, and others which will be apparent to those of skill in the art in view of the disclosure herein. Aspiration pump 50 may alternatively be a manually activated pump such as a syringe.

In some applications, it may be desirable to provide a non occlusive restriction of flow between the vacuum canister 58 and the flow control module 28. A flow restrictor may be coupled such as by luer connectors in series with the vacuum line 40. In one implementation the flow restrictors enables toggling between a low flow and a high flow configuration. The flow restrictors may comprise a variable restrictor that may be adjusted by a user. This may be accomplished by selectively diverting flow between a relatively smaller diameter and larger diameter aperture, a variable diameter aperture, or other flow regulators such as any of those disclosed in the United States patent publication No. 2021/0315597 to Buck, et al, entitled Aspiration System with Accelerated Response, the disclosure of which is hereby incorporated in its entirety herein.

In one particular implementation, a rotatable drum is provided with a first transverse flow path having a first diameter. The drum is rotatable within a housing having an inlet port and an outlet port. The drum may be rotated to place the inlet port into fluid communication with the outlet port through the first flow path. A second flow path having a second, different diameter also extends transversely through the drum, rotationally offset from the first flow path. The drum may be rotated to place the inlet port into communication with the outlet port through the second flow path, thereby providing a flow rate through the drum different from the flow rate provided by the first flow path.

The filter chamber 33 on the flow control module 28 or on the connector module 30 is spaced apart from the remote vacuum pump 42 and vacuum canister 58 to provide enhanced aspiration performance. Conventional aspiration pumps and filters are intended to be placed outside of the sterile field and may be far enough away from the patient to require a length of aspiration tubing 40 between the pump assembly 42 and the catheter 12 to be at least about 50 inches or about 100 inches or more. For example, the tubing 40 may be about 102 inches.

The pump typically includes an aspiration canister 58 for blood collection. When aspiration is desired in a prior art system, a valve is opened to place the low pressure canister 58 in communication with the catheter 12 by way of the aspiration tubing 40, to aspirate material from the patient. But the length of the aspiration tubing extending from inside to outside of the sterile field operates as a flow restrictor, causing a delay between the time of activating the vacuum button on the pump assembly 42 and actual application of suction to the clot at the distal end of the catheter.

In the illustrated implementation, the only flow restriction between a source of vacuum (filter chamber 33) and the patient is the relatively short aspiration pathway between the on/off valve in the handpiece actuated by toggle switch 48 and the distal end 18 of the catheter. When the aspiration control 48 is activated to open the flow path, the flow restriction and enclosed volume on the patient side of the filter chamber 33 is low relative to the flow restriction and enclosed volume through aspiration tubing 40 on the pump side of the filter chamber 33.

This dual chamber configuration produces a rapid spike in negative pressure experienced at the distal end 18 of the catheter 12 upon activation of the aspiration control 48, and rapid filling of the chamber 33. The response time between activating the aspiration control 48 and realizing suction actually experienced at the clot is significantly faster and allows significantly higher initial flow than the response time realized in a conventional system having only a vacuum chamber 58 located at the pump assembly 42 outside of the sterile field.

The spike of negative pressure experienced at the distal end of the catheter will fade as pressure equilibrium is reached between the filter chamber 33 and canister 58. When the aspiration control 48 is closed, the vacuum pump 50 will gradually bring the pressure in the filter chamber 33 back down to the level in the vacuum canister 58 at the pump.

Figure 4:
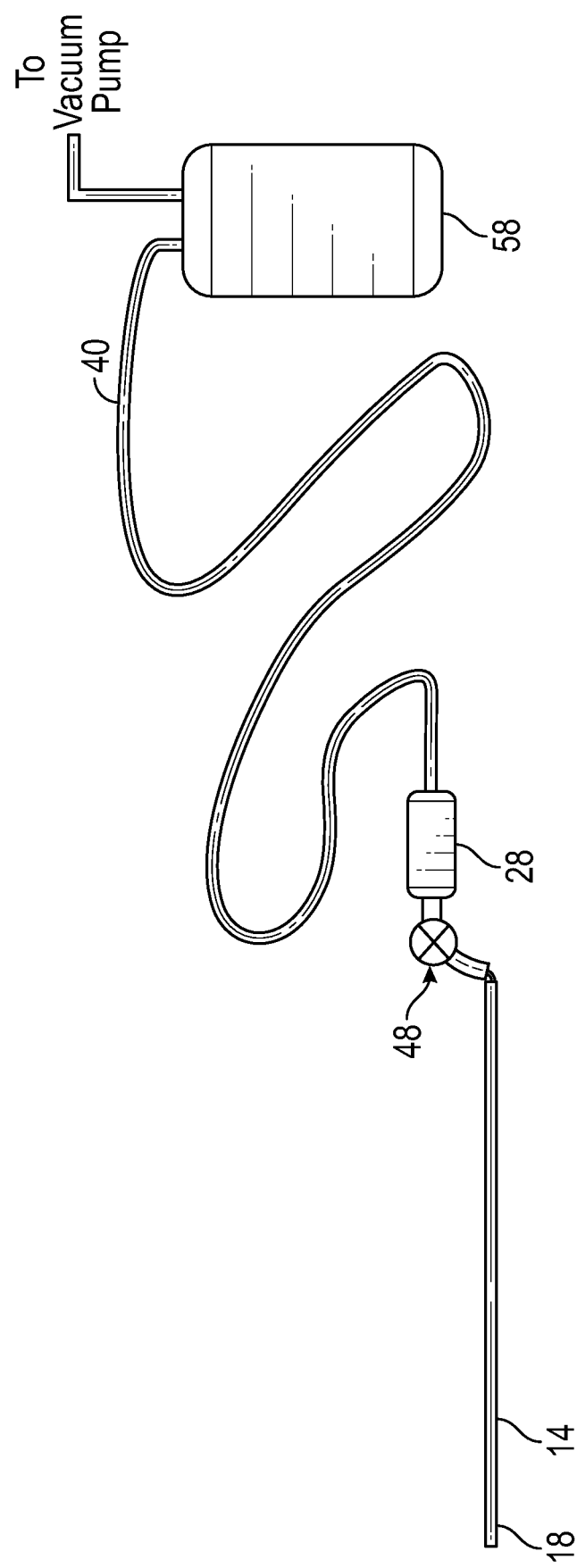
FIG. 4 is a schematic view of the dual vacuum chamber configuration that produces an accelerated aspiration response.
Figure 5:
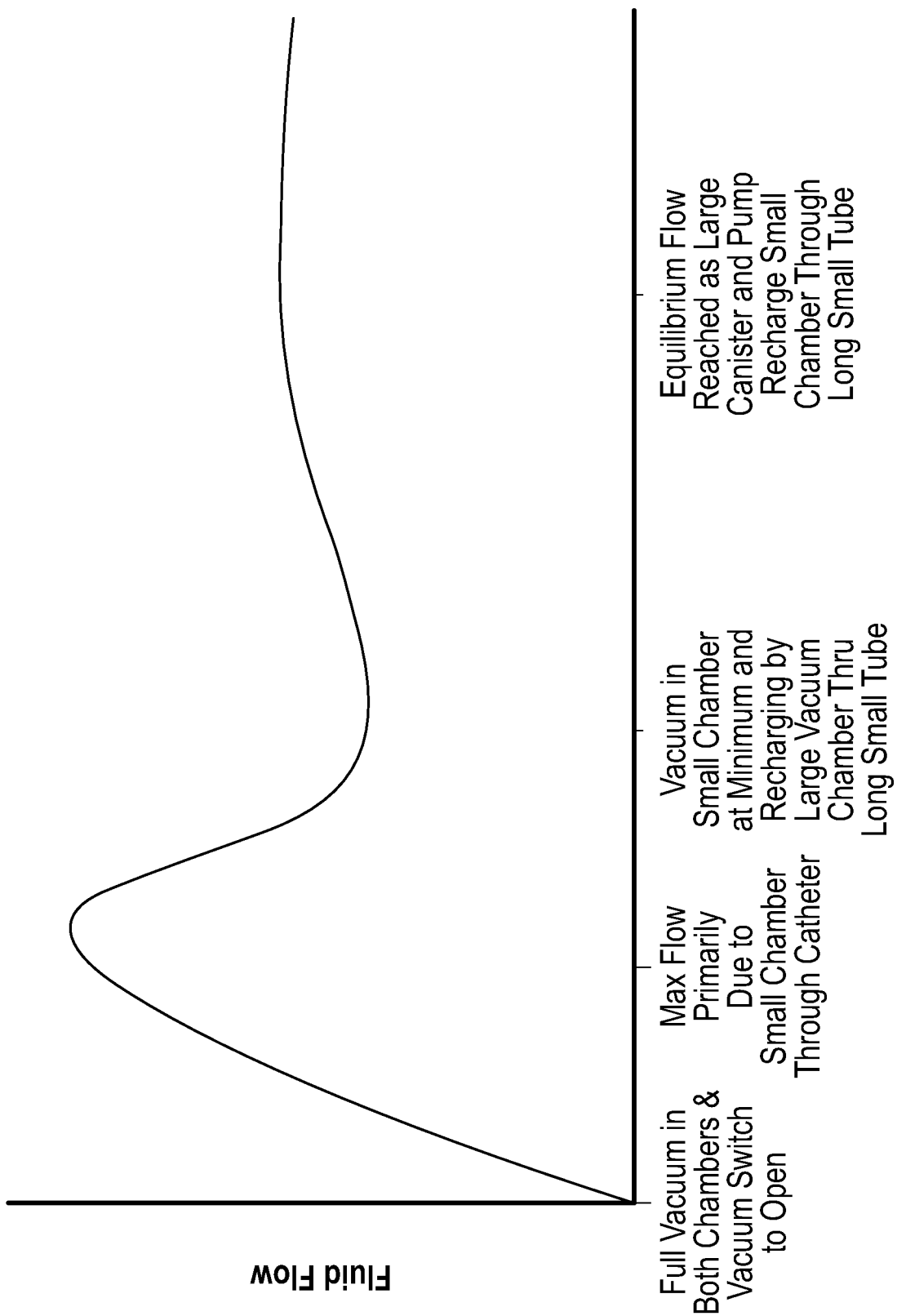
FIG. 5 is a qualitative fluid flow rate diagram at the catheter tip following opening of the vacuum control valve.

A simplified fluid flow diagram is illustrated in FIG. 4, and a qualitative flow rate diagram is illustrated in FIG. 5. The flow restriction between chamber 33 and the distal end 18 of catheter 12 is small relative to the flow restriction between the vacuum canister 58 and the vacuum chamber 33. This allows a negative pressure peak experienced at distal end 18 almost instantaneously upon activation of vacuum switch 48. The flow rate of material into the catheter 12 rapidly reaches a peak and subsides as vacuum chamber 33 fills with aspirated material. The vacuum in chamber 33 declines to a minimum, and slowly recharges by the large vacuum chamber 58 and associated pump through tubing 40 when the toggle switch 48 is moved into the closed position. In some instances of use, a clinician may choose to close the vacuum switch 48 at or shortly following the maximum flow rate, just giving a short burst or series of bursts of pulsatile vacuum to facilitate spiration of thrombus into the catheter 12. In use, a similar effect may be established by utilizing the vent 47. The vacuum in chamber 33 may decline to a minimum as the button 62 is actuated such that the vent is opened. Thereafter, the vacuum chamber 33 may slowly recharge by the large vacuum chamber 58 and associated pump through tubing 40 when the button 62 and vent 47 are moved into the closed position. In some instances of use, a clinician may choose to open the vent 47 at or shortly following the maximum flow rate, just giving a short burst or series of bursts of pulsatile vacuum to facilitate spiration of thrombus into the catheter 12.

If the application of vacuum is not able to aspirate the clot into the catheter, an elongate flexible thrombus engagement tool may be advanced through the aspiration catheter, to facilitate retrieval of the clot. The thrombus engagement tool may comprise an elongate flexible shaft having a proximal hand piece such as a knob configured to be rotated by hand. The distal end carries a clot engagement tip which may include one or more radially outwardly extending engagement structures such as a helical thread.

Figure 6A:
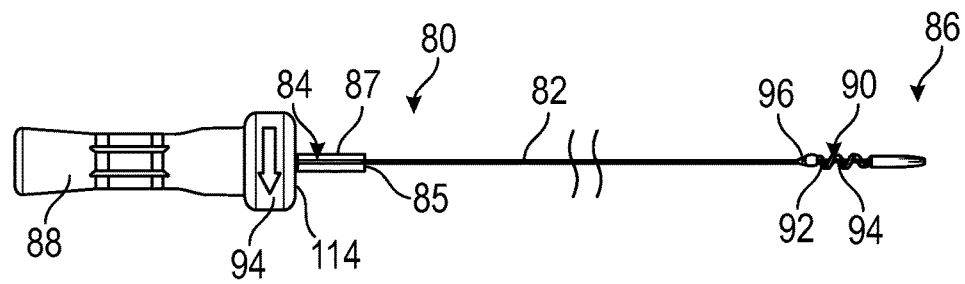
FIG. 6A is a side elevational view of a thrombus engagement tool.
Figure 6B:
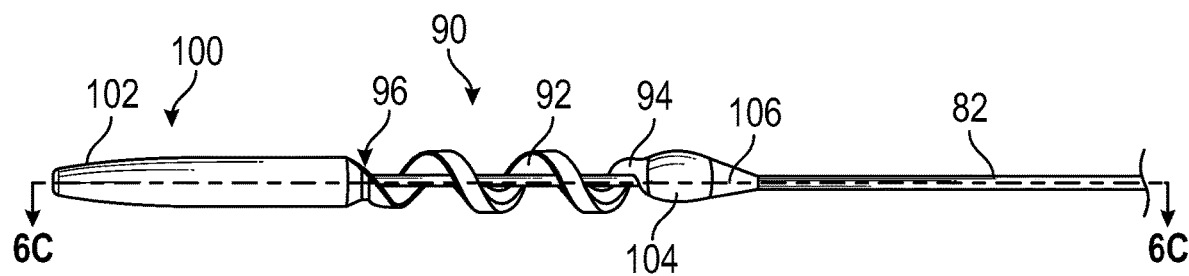
FIG. 6B is an enlarged detail view of the distal end of the thrombus engagement tool of FIG. 6A.
Figure 6C:
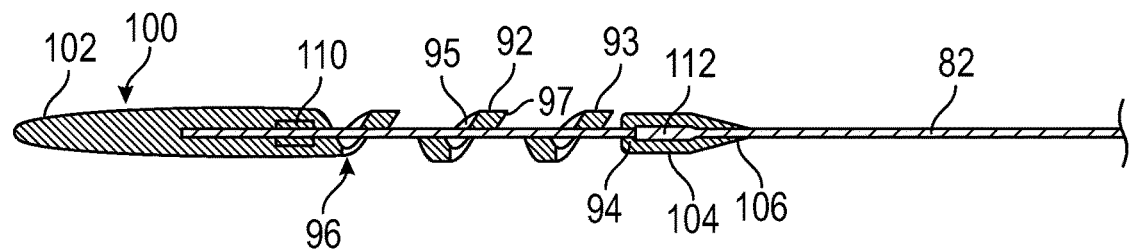
FIG. 6C is a longitudinal elevational cross-section through the thrombus engagement tool of FIG. 6B.

Referring to FIGS. 6A-6C, a thrombus engagement tool 80 may comprise an elongate flexible shaft 82 having a proximal end 84 and a distal end 86. A proximal hand piece such as a torquing handle 88 may be configured to be rotated by hand. Distal end 86 carries a clot engagement tip 90 which may include one or more radially outwardly extending structures such as a helical thread 92. The handle 88 may have an indicium of rotational direction such as a printed or molded arrow 94 which indicates the direction to rotate the handle 88 in order for the helical thread 92 to engage clot.

Referring to FIG. 6B, the distal tip 90 includes a helical thread 92 extending between a distal thread end 96 and a proximal thread end 94 and supported by flexible shaft 98. The axial length of the distal tip 90 is at least about 5 mm or 10 mm or 15 mm or 20 mm and in some embodiments no more than about 30 mm or 20 mm measured along the flexible shaft 98. Preferably, the axial length will be within the range of from about 20 mm to about 25 mm.

The helical thread 92 wraps around the axis at least about 1 or 2 or 4 or more full revolutions, but in some embodiments no more than about 10 or no more than about 6 revolutions. Preferably, the thread 92 wraps around the axis within the range of from about 2.5 to about 4.5 revolutions. In some embodiments the axial length along the threaded portion of the tip is within the range of from about 5 to about 15 mm, and preferably within the range of from about 8 mm to about 12 mm.

The helical thread 92 on this implementation may have a constant pitch throughout its length. The pitch may be within the range of from about 5 to about 10 threads per inch depending upon desired performance. For example, the thread to thread spacing in the axial direction may be within the range of from about 2 mm to about 6 mm, preferably from about 3 mm to about 4 mm.

Alternatively, the thread may have multiple pitches (e.g. stepped or graduated) designed to engage, transport or grasp thrombus within the catheter lumen. A distal pitch may be less than a proximal pitch. The pitch may vary continuously along the length of the thread, or may step from a first, constant pitch in a proximal zone to a second, different pitch in a distal zone of the thread. The thread 92 may comprise a continuous single helical flange or may have a plurality of discontinuities to produce a plurality of teeth or serrations, arranged helically around the core wire.

The maximum OD of the thread 92 is preferably smaller than the diameter of a sliding fit within the intended catheter lumen, and may generally be at least about 0.015 inches or at least about 0.010 inches smaller than the catheter lumen ID. In some implementations, the max OD of the tip may be significantly less than the inside diameter of the catheter lumen to allow more space for the thrombus along the side of the tip but still create significant grasping force via lateral engagement of the helical threads with the thrombus.

In one implementation, the maximum helical thread diameter is about 0.110 inches, and the catheter lumen ID is about 0.275 inches (24 F) (a 0.165 inch gap between the helical threads and catheter wall). In another implementation, the maximum OD of the tip is within the range of from about 0.03 to about 0.06 inches within a catheter having a distal end ID within the range from about 0.068 inches to about 0.073 inches. This leaves a substantial tip bypass flow path.

In certain applications, the max OD of the tip is no more than about 35% or no more than about 40% or no more than about 60% of the ID of the corresponding catheter and may be within the range of from about 35% to about 55% of the catheter ID. In some instances, the max OD of the tip may slightly less than the ID of the corresponding catheter to provide a sliding fit within the intended catheter lumen. For example, the max OD of the tip may be no less than about 90% or no less than about 95% or no less than about 97% of the ID of the corresponding catheter.

Since this implementation of the thrombus engagement tool does not have any centering structures for the tip 90 or shaft 82, the tip 90 will normally be pushed to one side of the aspiration lumen. When a clot becomes lodged between the tip 90 and the opposing inside surface of the side wall of the catheter, manual manipulation such as rotation of the tip 90 can engage the clot like a worm gear and either grasp the clot (e.g., by pinning it against the opposing catheter sidewall) for retraction or facilitate freeing the blockage and aid in ingestion of the clot into the catheter. Manual manipulation may also include axial proximal and distal reciprocation along with rotation, during aspiration, which can facilitate ingestion of the clot into the catheter.

Thus, an unimpeded flow path is created in the annular (if the tip were centered) space between the maximum OD of the tip, and the ID of the catheter lumen. This annular flow path cooperates with the vacuum and helical tip to grab and pull obstructive material into the catheter under rotation and vacuum. The annular flow path is significantly greater than any flow path created by manufacturing tolerances in a tip configured to shear embolic material between the tip and the catheter wall.

Additional aspiration volume is obtained as a result of the helical channel defined between each two adjacent threads of the tip. A cross sectional area of the helical flow path of a tip having a maximum OD in the range of from about 0.0400 to about 0.0406 inches will generally be at least about 0.0003 square inches, and in some embodiments at least about 0.00035 or at least about 0.000375 inches. The total aspiration flow path across the helical tip is therefore the sum of the helical flow path through the tip and the annular flow path defined between the OD of the tip and the ID of the catheter lumen.

Aspiration occurs both through the helical channel formed between adjacent helical threads as well as around the outside of the tip such that the assembly is configured for engaging and capturing embolic material but not shearing it between a sharp edge of the thread and the inside wall of the catheter.

The distal advance segment 100 advantageously permits the thrombus engagement device 80 to at least partially move past the thrombus without "pushing" the thrombus in a distal direction as the tip 90 is advanced. This may inhibit the thrombus (or any particulate thereof) from passing downstream within the vessel during engagement of the device 80 with the thrombus.

In some instances, the distal advance segment 100 can comprise a continuation of the helical thread 92. For example, the distal advance segment 100 may comprise a threaded segment continuing from the helical thread 92. The threaded distal advance segment 100, in some instances, may maintain an outer diameter consistent with the remainder of the helical thread 92. The threaded distal advance segment 100, in some instances, may comprise a thread that tapers in a distal direction towards a smaller outer diameter relative to the remainder of the helical thread 92. For example, the helical thread 92 may comprise a proximal cylindrical segment and a distal tapered segment that extends along the distal advance segment 100.

The profile of the tip 90 in an end view along the axis of rotation may be circular and/or, in some instances, may vary to create a non circular pattern around the axis of rotation. For example, profile may comprise a helical pattern, such as an oval cross-section that rotates along the axis of rotation to create the helical profile. The tip as seen in an end elevational view thus may exhibit a major diameter and a minor diameter. The minor diameter may be no more than about 95% or 90% or 80% or 70% of the major diameter, depending upon desired performance. In the illustrated example, the outer edge 93 of the thread 92 lies along the surface of a cylinder.

In the illustrated implementation, an outer edge 93 of the thread 92 thus has a linear surface in the axial direction, substantially conforming to the surface of a cylinder. A distal side 95 of the thread 92 is inclined radially outwardly in a proximal direction. A proximal side 97 of the thread 92 also inclines radially outwardly in a proximal direction thereby defining a proximally facing undercut along the length of the thread.

Referring to FIGS. 6B and 6C, the illustrated tip 90 includes an atraumatic, tapered distal advance segment 100 extending between an atraumatic distal tip at 102 and a transition to the distal end 96 of the thread 92. Helical thread 92 extends proximally from the transition to a proximal end 94 of the helical thread 92. In some instances, a trailing segment 104 may extend between the proximal end 94 of the thread and the proximal end 106 of the tip.

The axial length of the distal advance segment 100 may be at least about 5 mm or at least about 8 mm or 9 mm and generally less than about 15 mm, and in some implementations is within the range of from about 8 mm to about 12 mm.

The outside diameter of the flexible shaft 82 is generally less than about 0.02 inches, or less than about 0.015 inches and, in one implementation, is about 0.008 inches. In some instances, the flexible shaft 82 may comprise a distal tapered section. The distal tapered section may advantageously increase tip flexibility and/or maximize aspiration. The outside diameter at the distal end of the distal tapered section of the flexible shaft 82 is generally less than about 0.01 inches, or less than about 0.008 inches and, in one implementation, is no more than about 0.006 inches.

The outside diameter of the advance segment 100 at distal tip 102 is generally less than about 0.024 inches, or less than about 0.020 inches and, in one implementation, is about 0.018 inches. The maximum outside diameter of the advance segment 100 and helical thread 92 may be within the range from about 0.020 to about 0.045 inches, and, in one implementation, is less than about 0.040 inches, such as about 0.035 inches. The advance segment, helical thread and trailing segment of the tip 90 may be molded as a single piece over the flexible shaft 82 using any of a variety of polymers known in the catheter arts.

Referring to FIG. 6C, a first radiopaque marker 110 may be carried on the flexible shaft 82 beneath the advance segment 100. A second radiopaque marker 112 may be carried on the flexible shaft 82 within the trailing segment 104. Each radiopaque marker may comprise a radiopaque tube or a coil of radiopaque wire such as a platinum iridium alloy wire having a diameter about 0.002 inches and positioned or wrapped around the flexible shaft 82 and soldered to the flexible shaft 82 to produce an RO sleeve or coil having an outside diameter of less than about 0.020 inches, such as about 0.012 inches. The radiopaque markers may also provide an axial interference fit between the flexible shaft 82 and the advance segment 100 and trailing segment 104 to resist core wire axial pull out from the tip 90 (tip detachment).

In certain implementations, the maximum OD of the thread 92 exceeds the maximum OD of the advance segment 100 by at least about 15% or 25% or 30% or more of the OD of the advance segment 100, to facilitate crossing the clot with the advance segment 100 and engaging the clot with the thread 92.

Depending upon the clinical application, it may be desirable to control the extent to which, if any, the distal tip 102 can extend beyond the distal end of the catheter 12. In certain implementations, the distal tip 102 may be permitted to extend at least about 2 cm or 3 cm and preferably as much as 4 to 8 cm beyond the catheter (such as to permit manual removal of engaged thrombus), but generally will be limited to extend no more than a preset distance such as 12 cm or 8 cm or 5 cm beyond the catheter (e.g., within the range of from about 5 cm to about 10 cm) depending upon desired performance.

Distal advance of the tip 102 may be limited by providing mechanical interference at the desired distal limit of travel. In one implementation, a distal stop surface 114 which may be on the handle 88 (see FIG. 6A) provides an interference engagement with a complementary proximal surface (e.g. proximal surface 33 on connector module 30 or on the catheter hub) carried by the aspiration catheter through which the thrombus engagement tool 80 is advanced. Alternatively, a distal engagement surface can be carried anywhere along the length of the thrombus engagement tool 80, for sliding rotational engagement with a complementary proximally facing stop surface carried by the catheter. Additional details of distal limit configurations may be found in U.S. patent application Ser. No. 17/036,258 filed Sep. 29, 2020 and entitled Embolic Retrieval Catheter, which is hereby expressly incorporated in its entirety herein by reference.

The limit on distal advance of the helical tip may enable a first configuration in which the distal tip may be advanced through the catheter and placed at a first position approximately aligned with the distal end of the catheter 12. The physician may then advance the tip to a second position extending beyond the distal end of the catheter such as for inspection and cleaning purposes.

A position indicator 85 may be carried by the flexible shaft 82 spaced apart from the distal surface 114 by a distance corresponding to the maximum length of the thrombus engagement tool intended to extend beyond the distal end of the catheter. When the position indicator 85 is located at a corresponding reference point relative to the catheter hub, the distal tip 102 may be positioned approximately at the distal end of the catheter. This way the physician will know that any further distal advance of the thrombus engagement tool will be extending beyond the distal end of the catheter. The maximum extension will be reached when the distal surface 114 contacts the catheter hub.

The position indicator 85 may comprise any of a variety of visual or tactile features, such as a color change or a colored band surrounding the flexible shaft 82. In a visual indicium implementation (color change or circumferential line) the distal tip 102 may be positioned approximately at the distal end of the catheter when the indicator is visible just outside of the hub. In another implementation, the position indicator 85 comprises the transition between the distal end of the hypo tube 87 and the underlying flexible shaft 82. This provides haptic feedback as the indicator (step in outside diameter) encounters and passes through the valve of the RHV. The hypo tube 87 additionally functions as a strain relief or anti buckling feature and may have an axial length within the range of from about 3 cm to about 15 cm and in some implementations within the range of from about 5 cm to about 9 cm.

Figure 7A:
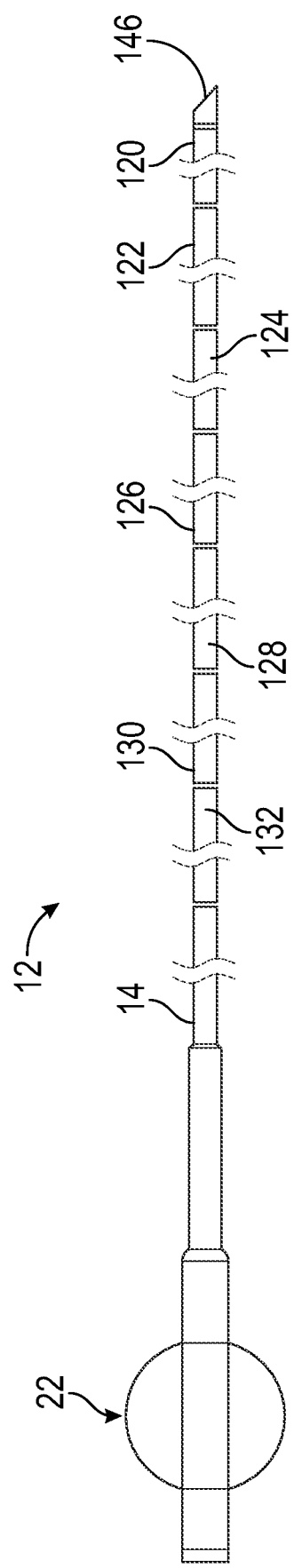
FIGS. 7A-7E are side elevational views of various embodiments of thrombectomy catheters.
Figure 7B:
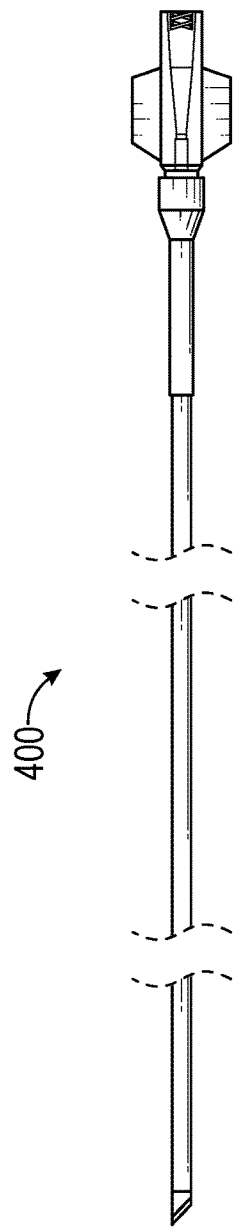
Figure 7C:
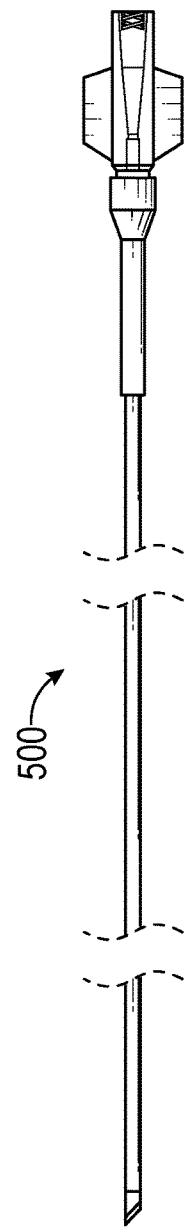
Figure 7D:
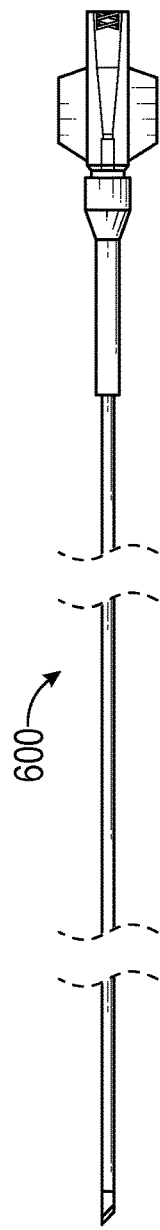

Referring to FIG. 7A, there is illustrated one example of an outer jacket segment stacking pattern for a progressive flexibility catheter of the type discussed in connection with FIG. 1. A distal segment 120 may have a length within the range of about 1-3 cm and a durometer of less than about 35 D or 30 D. An adjacent proximal segment 122 may have a length within the range of about 4-6 cm, and a durometer of less than about 35 D or 30 D. An adjacent proximal segment 124 may have a length within the range of about 4-6 cm, and a durometer of about 35 D or less. An adjacent proximal segment 126 may have a length within the range of about 1-3 cm, and a durometer within the range of from about 35 D to about 45 D (e.g., 40 D). An adjacent proximal segment 128 may have a length within the range of about 1-3 cm, and a durometer within the range of from about 50 D to about 60 D (e.g., about 55 D). An adjacent proximal segment 130 may have a length within the range of about 1-3 cm, and a durometer within the range of from about 35 D to about 50 D to about 60 D (e.g., about 55 D). An adjacent proximal segment 132 may have a length within the range of about 1-3 cm, and a durometer of at least about 60 D and typically less than about 75 D. More proximal segments may have a durometer of at least about 65 D or 70 D.

The distal most two or three segments may comprise a material such as Tecothane and/or PEBAX, and more proximal segments may comprise PEBAX or other catheter jacket materials known in the art. At least three or five or seven or nine or more discrete segments may be utilized, having a change in durometer between highest and lowest along the length of the catheter shaft of at least about 10 D, preferably at least about 20 D and in some implementations at least about 30 D or 40 D or more.

FIGS. 7A-7E illustrate various embodiments of catheters, at least some of which incorporate a plurality of catheter outer jacket segments with varying lengths and/or hardness for varying flexibility along the length of the catheter body. It will be understood that any of the features shown or described in connection with any of the catheters of FIGS. 7A-7E can be used with any of the embodiments described and/or contemplated herein. It will also be understood that any of the features described and/or contemplated in connection with any of the embodiments disclosed herein can be utilized with any of the catheters described in connection with FIGS. 7A-7E. As with all embodiments in this specification, any feature, structure, material, method, or step that is described and/or illustrated in the embodiments of FIGS. 7A-7E can be used with or instead of any feature, structure, material, method, or step that is described and/or illustrated in any other embodiment of this specification.

Figure 7E:
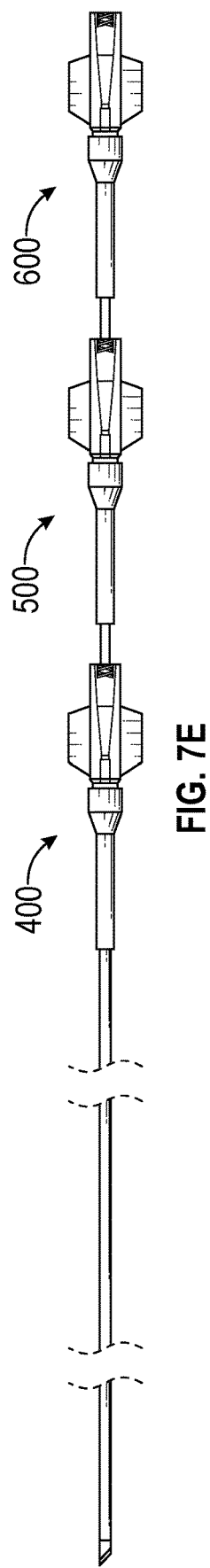

FIGS. 7B-7E illustrates embodiments of various catheters 400, 500, 600. The catheters 400, 500, 600 may include differing properties (e.g., such as length, diameter, etc.) such that one or more of the catheters 400, 500, 600 may interact with any of the other catheters 400, 500, 600 in any various manner. In one instance, as illustrated by FIG. 7E, each of catheters 400, 500, 600 may comprise a different size to permit the catheters 400, 500, 600 to at least partially extend through one or more of the other catheters 400, 500, 600. The lengths of each of the catheters 400, 500, 600 may vary so as to permit a smaller catheter to pass through and extend distally beyond a larger catheter in a telescoping manner.

For instance, catheter 500 may be configured to pass through and extend beyond catheter 400. By way of further example, catheter 600 may be configured to pass through and extend beyond at least one of catheter 500 or catheter 400 in a telescoping manner. While FIG. 7E illustrates an example telescoping catheter stack including each of catheters 400, 500, 600, it will be understood by one having skill in the art that any combination of catheters 400, 500, 600 may be utilized. For example, a system may incorporate the use of catheter 400 and catheter 500, the use of catheter 400 and catheter 600, or the use of catheter 500 and catheter 600.

Catheter 400 may comprise an 8 F catheter. In some instances, catheter 400 comprises a diameter larger than the diameter of any of the remaining catheters in a system. Additionally, or alternatively, catheter 400 may comprise an overall length shorter than the length of any of the remaining catheters in a system. In this manner, catheter 400 may comprise the outermost catheter in a telescoping system and may permit any of the remaining catheters 500, 600 to extend distally beyond a distal end of catheter 400. The catheter 400 may comprise a length between about 35 cm and about 105 cm or, a length between about 45 cm and about 95 cm. The catheter 400 may comprise a length of from about 50 cm to about 90 cm. The catheter 400 may comprise a length at least shorter than any catheter with a diameter smaller than catheter 400 (e.g., such as catheter 500, 600).

Catheter 500 may comprise a 6 F catheter. In some instances, catheter 500 comprises a diameter in between the diameters of the remaining catheters in a system. Additionally, or alternatively, catheter 500 may comprise a length in between the lengths of the remaining catheters in the system. In this manner, catheter 500 may comprise a middle catheter in a telescoping system and may be configured to pass through and extend beyond one or more catheters while also permitting another catheter to extend distally beyond a distal end of catheter 500. The catheter 500 may comprise a length between about 120 cm and about 155 cm or between about 130 cm and about 145 cm. The catheter 500 may comprise a length of about from 135 cm to about 137 cm. The catheter 500 may comprise a length at least longer than any catheter with a diameter larger than catheter 500 (e.g., such as catheter 400). The catheter 500 may comprise a length at least shorter than any catheter with a diameter smaller than catheter 500 (e.g., such as catheter 600).

Catheter 600 may comprise a 5 F catheter. In some instances, catheter 600 comprises a diameter smaller than the diameters of the remaining catheters in a system. Additionally, or alternatively, catheter 600 may comprise a length longer than the lengths of any of the remaining catheters in the system. In this manner, catheter 600 may comprise an innermost catheter in a telescoping system and may be configured to pass through and extend beyond one or more of the other catheters. The catheter 600 may comprise a length between about 145 cm and about 175 cm or between about 155 cm and about 165 cm. The catheter 600 may comprise a length of about 160 cm. The catheter 600 may comprise a length at least longer than any catheter with a diameter larger than catheter 600 (e.g., such as catheter 400, 500).

One or more of the catheters 400, 500, 600 may include a coil and/or a braid in the sidewall extending through at least a portion of the sidewall of the catheter 400, 500, 600, as discussed herein. The braid may have properties that vary along the length of each catheter 400, 500, 600 to generate a variety of desired characteristics of the catheter 400, 500, 600. For example, a wire density of the braid may vary gradually or in steps along the length of the catheter 400, 500, 600 and/or vary between discrete sections of the catheter 400, 500, 600.

Catheter 600 may comprise one or more discrete sections with braid properties varying between one or more of the sections. In some instances, catheter 600 may comprise a first section, a second (e.g., intermediate) section, and a third distal section. However, it will be understood by one having skill in the art that the catheter 600 may comprise a fewer number of sections (e.g., one section or two sections) or a greater number of sections (e.g., four sections or greater). A sidewall property, such as a length and/or a wire density the braid along a respective section, may vary between the sections. In some instances, a pics per inch (ppi) count of the braid in connection with the wire density of the braid may gradually transition between one or more of the catheter sections. For example, the ppi count of the braid, in some instances, may remain generally consistent through a length of the first section and a length of the third section but gradually transition along the length of the second, intermediate section.

The first section of catheter 600 may have a length of at least about 20 cm. For example, the length of the first section may be from about 25 cm to about 35 cm or, in one example, about 30 cm. The braid through the first section may have a wire density of at least about 100 ppi. For example, the braid through the first section may have wire density of at least about 120 ppi or, more specifically, about 130 ppi.

The third section of catheter 600 may have a length of at least about 100 cm. For example, the length of the third section may be from about 120 cm to about 140 cm or, more specifically, about 130 cm. The braid through the third section may have a wire density of no greater than about 85 ppi. For example, the braid through the third section may have wire density from about 70 ppi to about 80 ppi.

The second section of catheter 600 may be an intermediate section between the first section and the third section. The second section may have a length of at least about 3 cm. In some instances, the second section may have a length no greater than about 20 cm or, more specifically, no greater than about 10 cm. For example, the length of the second section may be about 5 cm. The braid through the second section may have a wire density of no greater than the wire density of the first section and no less than the wire density of the third section.

Catheter 500 may comprise one or more discrete sections with braid properties varying between one or more of the sections. In some instances, catheter 500 may comprise a first section, a second (e.g., intermediate) section, and a third section. However, it will be understood by one having skill in the art that the catheter may comprise a fewer number of sections (e.g., one section or two sections) or a greater number of sections (e.g., four sections or greater). A sidewall property, such as a length and/or a wire density the braid along a respective section, may vary between the sections. In some instances, a ppi count of the braid in connection with the wire density of the braid may gradually transition between one or more of the catheter sections. For example, the ppi count of the braid, in some instances, may remain generally consistent through a length of the first section and a length of the third section but gradually transition along the length of the second, intermediate section.

The first section of catheter 500 may have a length of at least about 20 cm. For example, the length of the first section may be from about 25 cm to about 35 cm or, in one example, about 30 cm. The braid through the first section may have a wire density of at least about 100 ppi. For example, the braid through the first section may have wire density of at least about 120 ppi or, in one example, about 130 ppi.

The third section of catheter 500 may have a length of at least about 80 cm. For example, the length of the third section may be from about 100 cm to about 120 cm or, in one example, about 105 cm. The braid through the third section may have a wire density of no greater than about 100 ppi. For example, the braid through the third section may have wire density from about 80 ppi to about 90 ppi.

The second section of catheter 600 may be an intermediate section between the first section and the third section. The second section may have a length of at least about 3 cm. In some instances, the second section may have a length no greater than about 20 cm or, more specifically, no greater than about 10 cm. For example, the length of the second section may be about 5 cm. The braid through the second section may have a wire density of no greater than the wire density of the first section and no less than the wire density of the third section.

Catheter 400 may comprise one or more discrete sections with braid properties varying between one or more of the sections. In some instances, catheter 400 may comprise one section. However, it will be understood by one having skill in the art that the catheter 400 may comprise a greater number of sections (e.g., two sections, three sections, four sections, or greater). For example, catheter 400 may comprise three sections as described in connection with either one or catheter 500 or catheter 600. A sidewall property, such as a length and/or a wire density the braid, may vary along catheter 400. In some instances, a ppi count of the braid in connection with the wire density of the braid may gradually transition to increasing flexibility in a distal direction along catheter 400. The section of catheter 400 may have a length of at least about 40 cm. For example, the length of the section may be from about 50 cm to about 60 cm or, in one example, about 55 cm. The braid through the section may have a wire density of at least about 80 ppi. For example, the braid through the section may have wire density of at least about 90 ppi.

The braid, in some instances, may extend along an entire length of the catheter sidewall. In some instance, a junction between the braid and a coil is not present in the catheter and/or the catheter sidewall does not incorporate a coil. It will be understood that this braid configuration may be applied to any catheter disclosed herein, including, but not limited to, catheters 400, 500, 600.

One or more of the catheters 400, 500, 600 may an outer jacket segment stacking pattern for a progressive flexibility catheter. The outer jacket segment may each have properties that vary along the length of each catheter 400, 500, 600 to generate a variety of desired characteristics of the catheter 400, 500, 600. For example, each segment of the outer jacket may have a corresponding Shore D hardness to vary the flexibility along the length of the catheter 400, 500, 600. The outer jacket segments may be made of a thermoplastic elastomer made of flexible polyether and rigid polyamide (e.g., Pebax®). In some instances, each segment of the outer jacket may comprise a different variation of the thermoplastic elastomer to alter flexibility.

Catheter 600 may comprise a plurality of discrete segments of the outer jacket with varying flexibility between one or more of the segments. In some instances, catheter 600 may comprise a plurality of segments. A sidewall property, such as Shore D hardness and/or flexibility, may vary between the segments. In some instances, a Shore D hardness of the outer jacket segments may gradually transition from higher at proximal end segment of the outer jacket to lower at a distal end segment of the outer jacket.

The proximal end segment of the outer jacket of the catheter 600 may have a Shore D hardness of at least about 60. For example, the Shore D hardness of the proximal end segment may be from about 70 to about 80 or, more specifically, at least about 75.

The distal end segment of the outer jacket of the catheter 600 may have a Shore D hardness of at most about 40. For example, the Shore D hardness of the distal end segment may be from about 30 to about 20 or, more specifically, no more than about 27.

A plurality of the intermediate segments between the distal end segment and the proximal end segment may each comprise a variety of Shore D hardness. In some instances, each segment decreases in a Shore D hardness in a distal direction and may have a smaller Shore D hardness than a proximally adjacent segment. For example, the Shore D hardness of a first segment may be from about 30 to about 50 or, more specifically, about 40. The first segment, in some instances, may be between positioned about 120 cm to about 160 cm or, more specifically, about 140 cm away from a distal end face of the catheter 600. By way of another example, the Shore D hardness of the second segment may be from about 50 to about 70 or, more specifically, about 65. The second segment, in some instances, may be between positioned about 220 cm to about 260 cm or, more specifically, about 240 cm away from a distal end face of the catheter 600.

Catheter 500 may comprise a plurality of discrete segments of the outer jacket with varying flexibility between one or more of the segments. In some instances, catheter may comprise a plurality of segments. A sidewall property, such as Shore D hardness and/or flexibility, may vary between the segments. In some instances, a Shore D hardness of the outer jacket segments may gradually transition from higher at a proximal end segment of the outer jacket to lower at a distal end segment of the outer jacket.

The proximal end segment of the outer jacket of the catheter 500 may have a Shore D hardness of at least about 60. For example, the Shore D hardness of the proximal end segment may be from about 70 to about 80 or, more specifically, at least about 75.

The distal end segment of the outer jacket of the catheter 500 may have a Shore D hardness of at most about 40. For example, the Shore D hardness of the distal end segment may be from about 30 to about 20 or, more specifically, no more than about 27.

a plurality of the intermediate segments between the distal end segment and the proximal end segment may each comprise a variety of Shore D hardness. In some instances, each segment decreases in a Shore D hardness in a distal direction and may have a smaller Shore D hardness than a proximally adjacent segment. For example, the Shore D hardness of a first segment may be from about 30 to about 50 or, more specifically, about 40. The first segment, in some instances, may be between positioned about 70 cm to about 110 cm or, more specifically, about 90 cm away from a distal end face of the catheter 500. By way of another example, the Shore D hardness of a second segment may be from about 50 to about 70 or, more specifically, about 65. The second segment, in some instances, may be between positioned about 160 cm to about 200 cm or, more specifically, about 180 cm away from a distal end face of the catheter 500.

Catheter 400 may comprise a plurality of discrete segments of the outer jacket with varying flexibility between one or more of the segments. In some instances, catheter 400 may comprise a plurality of segments. A sidewall property, such as Shore D hardness and/or flexibility, may vary between the segments. In some instances, a Shore D hardness of the outer jacket segments may gradually transition from a proximal end segment of the outer jacket to a distal end segment of the outer jacket.

The proximal end segment of the outer jacket of the catheter 400 may have a Shore D hardness of at least about 60. For example, the Shore D hardness of the proximal end segment may be from about 70 to about 80 or, more specifically, about 75.

The distal end segment of the outer jacket of the catheter 400 may have a Shore D hardness of at most about 40. For example, the Shore D hardness of the distal end segment may be from about 30 to about 20 or, more specifically, no more than about 27.

A plurality of the intermediate segments between the distal end segment and the proximal end segment may each comprise a variety of Shore D hardness. In some instances, each segment decreases in a Shore D hardness in a distal direction and may have a smaller Shore D hardness than a proximally adjacent segment. For example, the Shore D hardness of a first segment may be from about 30 to about 50 or, more specifically, about 40. A first segment, in some instances, may be between positioned about 65 cm to about 105 cm or, more specifically, about 85 cm away from a distal end face of the catheter 400. By way of another example, the Shore D hardness of a second segment may be from about 40 to about 65 or, more specifically, about 55. The second segment, in some instances, may be between positioned about 105 cm to about 145 cm or, more specifically, about 125 cm away from a distal end face of the catheter 400. By way of further example, the Shore D hardness of a third segment may be from about 60 to about 80 or, more specifically, about 70. The third segment, in some instances, may be between positioned about 140 cm to about 180 cm or, more specifically, about 160 cm away from a distal end face of the catheter 400.

Catheter 400 may comprise a tubular body length of about 90+/−5 cm. In some instances, catheter 400 may comprise a tubular body length of about 50+/−5 cm. A number of the plurality of discrete segments of the outer jacket of catheter 400 may vary with respect to the tubular body length of catheter 400. A length of the respective segments of the plurality of discrete segments of the outer jacket of catheter 400 may vary with respect to the tubular body length of catheter 400.

A coating, in some instances, may be located along an outer diameter of a distal portion of the catheter sidewall. The coating can be configured to decrease frictional resistance of the distal portion of the catheter sidewall with any adjacent structure (e.g., a vessel wall). In some instances, the coating increases the lubriciousness of the catheter distal portion outer sidewall. The coating may advantageously reduce friction on the distal end of the catheter going through tortuous vasculature. This may facilitate advancement and rotation of the catheter distal end, particularly in situations where the catheter contains an increased flexibility along a distal end portion of the catheter. The coating may extend in a proximal direction from, or proximate to, a catheter distal end face. The coating may extend at least about 20 cm in a proximal direction. In some instances, the coating extends no farther than about 50 cm from the catheter distal end face. For example, the coating may extend for a length of about 25 cm to about 35 cm or, more specifically, about 30 cm from a catheter distal end face. It will be understood that the coating may be applied to any catheter disclosed herein, including, but not limited to, catheters 400, 500, 600.

Figure 8:
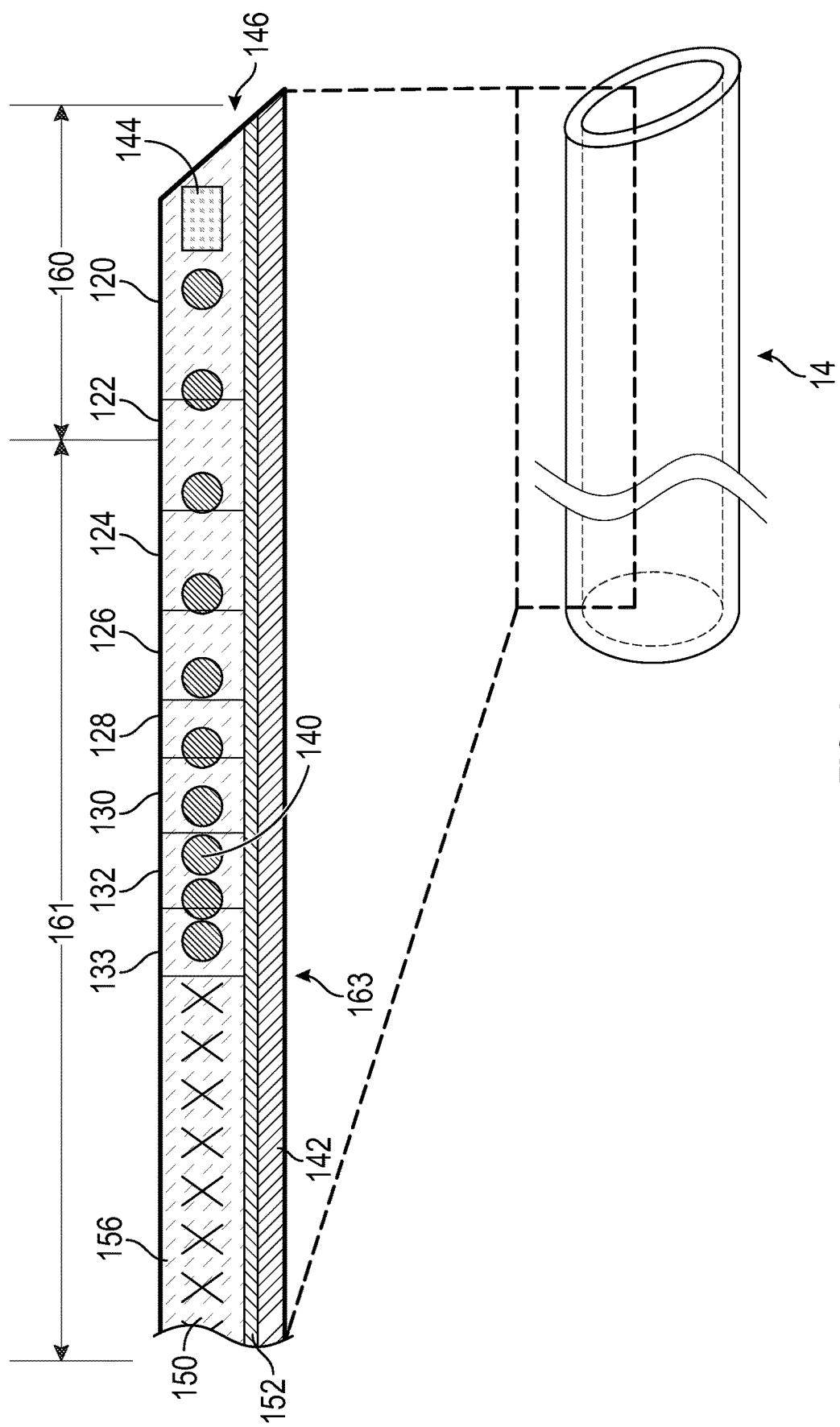
FIG. 8 is a cross-sectional view through a distal portion of the embolectomy catheter showing a side wall construction.

FIG. 8 illustrates a cross section through the sidewall of a distal portion of a single lumen catheter. An internal support layer may comprise either a coil or braid. In a coil implementation, adjacent loops or filars of the coil 140 may have a constant pitch throughout the length of the coil or may be closely tightly wound in a proximal zone with a distal section having looser spacing between adjacent loops. In an embodiment having a coil section 140 with an axial length of at least between about 20% and about 30% of the overall catheter length, (e.g., 28 cm coil length in a 110 cm catheter shaft 16), at least the distal about 1 cm or about 2 cm or about 3 cm or about 4 cm of the coil will have a spacing that is at least about 130%, and in some implementations at least about 150% or more than the spacing in the proximal coil section. In a 110 cm catheter shaft 3000 having a Nitinol coil, the spacing in the proximal coil may be about 0.004 inches and in the distal section may be at least about 0.006 inches or about 0.007 inches or more.

The distal end of the coil or braid 140 can be spaced proximally from the distal end of the inner liner 142, for example, to provide room for an annular radiopaque marker 144. The coil or braid 140 may be set back proximally from the distal end, in some embodiments, by approximately no more than about 1 cm, about 2 cm, or about 3 cm. In one embodiment, the distal end of the catheter 12 is provided with a beveled (inclined) distal surface 146 residing on a plane having an angle of at least about 10 degrees or about 20 degrees and in one embodiment about 30 degrees with respect to a longitudinal axis of the catheter 10. At least a distally facing edge of the annular radiopaque marker 144 may be an ellipse, residing on a plane which is inclined with respect to the longitudinal axis to complement the bevel angle of the distal surface 146. Additional details are described in connection with FIG. 9 below.

After applying a braid or braid and coil over tie layer 152 and/or over a liner, the distal braid or coil and the RO marker 144 are provided with an outer jacket 156 such as a polymer tube formed from a plurality of axially adjacent cylindrical segments to enclose the catheter body 16. The outer sleeve 156 may comprise any of a variety of materials, such as polyethylene, polyurethane, polyether block amide (e.g., PEBAX™), nylon or others known in the art. Sufficient heat is applied to cause the polymer to flow into and embed the proximal braid and distal coil.

In one implementation, the outer jacket 156 is formed by sequentially advancing a plurality of short tubular segments 133, 132, 130, 128, 126, 124, 122, 120 concentrically over the catheter shaft subassembly, and applying heat to shrink the sections on to the catheter 12 and provide a smooth continuous outer tubular body. The foregoing segmented construction may extend along at least the most distal about 10 cm, and preferably at least about the most distal about 20 cm, about 25 cm, about 30 cm, about 35 cm, about 40 cm, or more than about 40 cm of the catheter body 10. The entire length of the outer jacket 156 may be formed from tubular segments and the length of the distal tubular segments may be shorter than the one or more tubular segments forming the proximal portion of the outer jacket 156 proximal to the junction between the braid 150 and coil 140 in order to provide proximal backup support and steeper transitions in flexibility toward the distal end of the catheter 12.

The durometer of the outer wall segments may decrease in a distal direction. For example, proximal segments such as 133 and 132, may have a durometer of at least about 60 D or about 70 D, with gradual decrease in durometer of successive segments in a distal direction to a durometer of no more than about 35 D or about 25 D or lower. A 25 cm section may have at least about 3 or about 5 or about 7 or more segments and the catheter 12 overall may have at least about 6 or about 8 or about 10 or more distinct flexibility zones. The distal 1 or 2 or 4 or more segments 122, 120, may have a smaller OD following shrinking than the more proximal segments 133-124 to produce a step down in OD for the finished catheter body 16. The length of a lower OD section 160 may be within the range of from about 3 cm to about 15 cm and, in some embodiments, is within the range of from about 5 cm to about 10 cm such as about 7 cm or about 8 cm and may be accomplished by providing the distal segments 122, 120 with a lower wall thickness.

In another embodiment, the most distal portion of the catheter 12 may comprise a durometer of less than approximately 35 D (e.g., 25 D) to form a highly flexible distal portion of the catheter and have a length between approximately 25 cm and approximately 35 cm. The distal portion may comprise one or more tubular segments of the same durometer (e.g., segment 120). A series of proximally adjacent tubular segments may form a transition region between a proximal stiffer portion of the catheter 12 and the distal highly flexible portion of the catheter. The series of tubular segments forming the transition region may have the same or substantially similar lengths, such as approximately 1 cm.

The relatively short length of each of the series of tubular segments may provide a steep drop in durometer over the transition region. For example, the transition region may have a proximal tubular segment 122 (proximally adjacent the distal portion) having a durometer of approximately 35 D. An adjacent proximal segment 124 may have a durometer of approximately 55 D. An adjacent proximal segment 126 may have a durometer of approximately 63 D. An adjacent proximal segment 128 may have a durometer of approximately 72 D.

More proximal segments may comprise a durometer or durometers greater than approximately 72 D and may extend to the proximal end of the catheter. For instance, a catheter segment may comprise a proximal portion greater than approximately 72 D between about 1 cm and about 3 cm. In some embodiments, the proximal portion may be about 2 cm long. In some embodiments, the most distal segments (e.g., 120, 122) may comprise PEBAX™ and more proximal segments may comprise a generally stiffer material, such as Vestamid®.

The inner diameter of the catheter 10 may be between approximately 0.06 and 0.08 inches, between approximately 0.065 and 0.075 inches, or between approximately 0.068 and 0.073 inches. In some embodiments, the inner diameter is approximately 0.071 inches.

In some embodiments, the distal most portion may step or taper to a decreased inner diameter such as under segments 122 and 120. The taper may occur approximately between the distal highly flexible portion and the transition region (e.g., over the most proximal portion of the distal highly flexible portion). The taper may be relatively gradual (e.g., occurring over approximately 10 or more cm) or may be relatively steep (e.g., occurring over less than approximately 5 cm). The inner diameter may taper to an inner diameter between about 0.03 and about 0.06 inches. For example, the inner diameter may be about 0.035 inches, about 0.045 inches, or about 0.055 inches at the distal end of the catheter 12. In some embodiments, the inner diameter may remain constant, at least over the catheter extension segment.

In some hybrid coil/braid embodiments, the coil 140 may extend proximally from a distal end of the catheter 12 along the highly flexible distal portion ending at or overlapping with the distal end of the braid 150. In other embodiments, the coil 140 may extend the entire length of the catheter 12. The braid 150, when present, may extend from about the transition 163 the proximal end of the coil 140 to the proximal end of the catheter 12.

Figure 9:
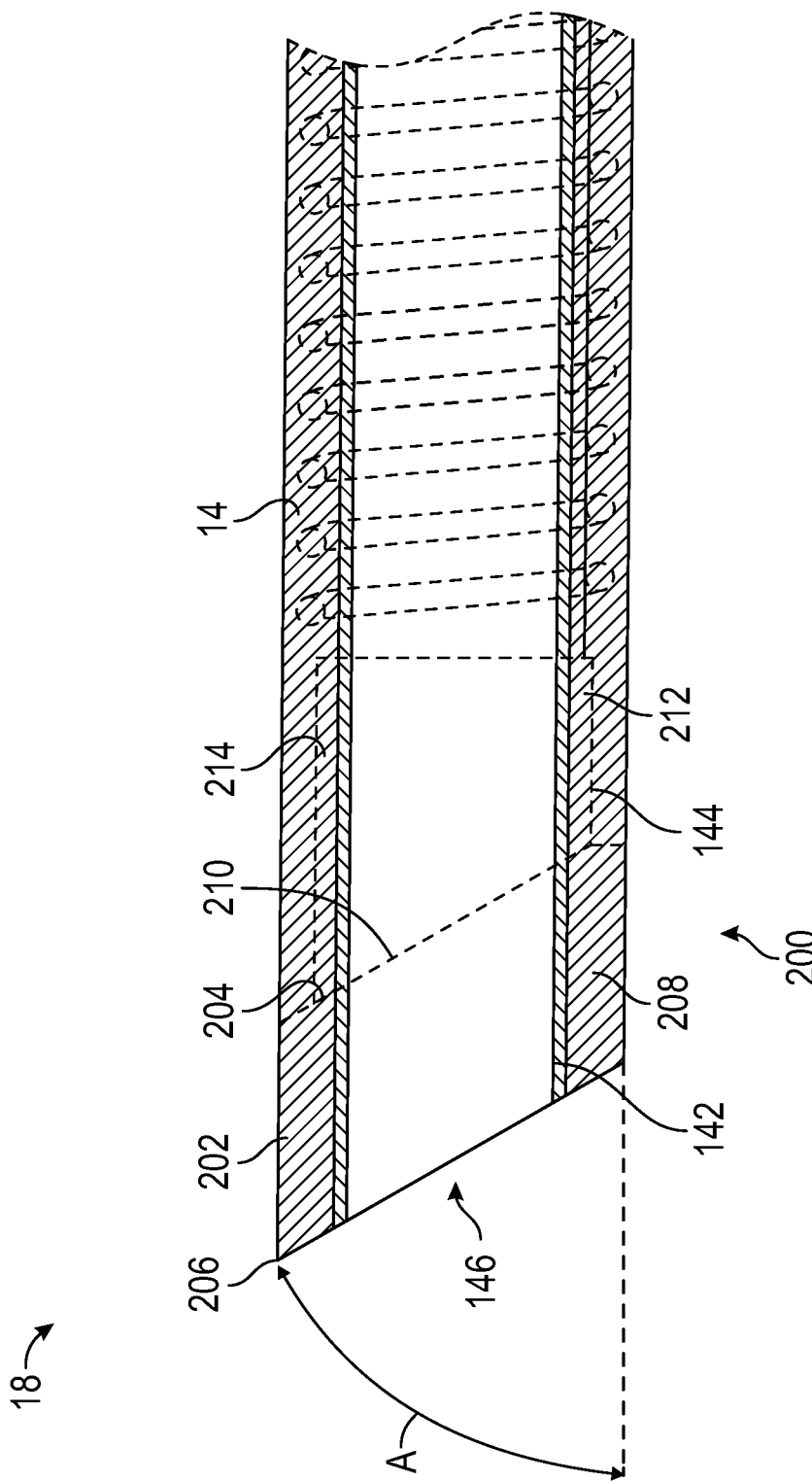
FIG. 9 is a cross-sectional view through a distal portion of the embolectomy catheter showing the radiopaque marker and inclined distal face.

Any of the catheters disclosed herein may be provided with an angled distal tip. Referring to FIG. 9, distal catheter tip 18 comprises a tubular body 14 which includes an advance segment 200, and a marker band 144. An inner tubular liner 142 may extend throughout the length of the distal catheter tip and may comprise dip coated PTFE.

A reinforcing element 140 such as a braid and/or spring coil is embedded in an outer jacket which may extend the entire length of the catheter proximally of the radiopaque marker.

The advance segment 200 terminates distally in an angled face 146, to provide a leading side wall portion 202 having a length measured between the distal end 204 of the marker band 144 and a distal tip 206. A trailing side wall portion 208 of the advance segment 200, has an axial length in the illustrated embodiment of approximately equal to the axial length of the leading side wall portion 202 as measured at approximately 180 degrees around the catheter from the leading side wall portion 202. The leading side wall portion 202 may have an axial length within the range of from about 0.1 mm to about 5 mm and generally within the range of from about 1 to 3 mm. The trailing side wall portion 208 may be at least about 0.1 or 0.5 or 1 mm or 2 mm or more shorter than the axial length of the leading side wall portion 202, depending upon the desired performance.

The angled face 146 inclines at an angle A within the range of from about 45 degrees to about 80 degrees from the longitudinal axis of the catheter. For certain implementations, the angle is within the range of from about 50 degrees to about 70 degrees or within the range of from about 55 degrees to about 65 degrees from the longitudinal axis of the catheter. In one implementation, the angle A is about 60 degrees. One consequence of an angle A of less than 90 degrees is an elongation of a major axis of the area of the distal port which increases the surface area of the port and may enhance clot aspiration or clot retention. Compared to the surface area of the circular, transverse port (angle A is 90 degrees), the area of the angled port is generally at least about 105%, and no more than about 130%, in some implementations within the range of from about 110% and about 125% and in one example is about 115%.

In the illustrated embodiment, the axial length of the advance segment is substantially constant around the circumference of the catheter, so that the angled face 146 is approximately parallel to the distal surface 210 of the marker band 144. The marker band 144 has a proximal surface approximately transverse to the longitudinal axis of the catheter, producing a marker band 144 having a right trapezoid configuration in a side elevational view. A short sidewall 212 is rotationally aligned with the trailing side wall portion 208, and has an axial length within the range of from about 0.2 mm to about 4 mm, and typically from about 0.5 mm to about 2 mm. An opposing long sidewall 214 is rotationally aligned with the leading side wall portion 202. Long sidewall 214 of the marker band 144 is generally at least about 10% or 20% longer than short sidewall 212 and may be at least about 50% or 70% or 90% or more longer than short sidewall 212, depending upon desired performance. Generally, the long sidewall 214 will have a length of at least about 0.5 mm or 1 mm and less than about 5 mm or about 4 mm.

Any of the marker bands described herein may be a continuous annular structure, or may optionally have at least one and optionally two or three or more axially extending slits throughout its length. The slit may be located on the short sidewall 212 or the long sidewall 214 or in between, depending upon desired bending characteristics. Any of the marker bands described herein may comprise any of a variety of radiopaque materials, such as a platinum/iridium alloy, with a wall thickness preferably no more than about 0.003 inches and in one implementation is about 0.001 inches.

The advance segment 200 may comprise a distal extension of the outer polymer jacket and optionally the inner liner, without other internal supporting structures distally of the marker band 144. The outer jacket may comprise extruded Tecothane and/or PEBAX. The advance segment 200 may have a bending stiffness and radial crush stiffness that is no more than about 50%, and in some implementations no more than about 25% or 15% or 5% or less than the corresponding value for the adjacent proximal catheter body.

The proximal end of the catheter 12 is preferably provided with a hemostasis valve, to facilitate introduction of a thrombus engagement tool or a secondary catheter there through. The hemostasis valve may be carried by the connector module 30, or directly by the proximal catheter connector 22. Any of a variety of hemostasis valve configurations may be used.

Figure 10A:
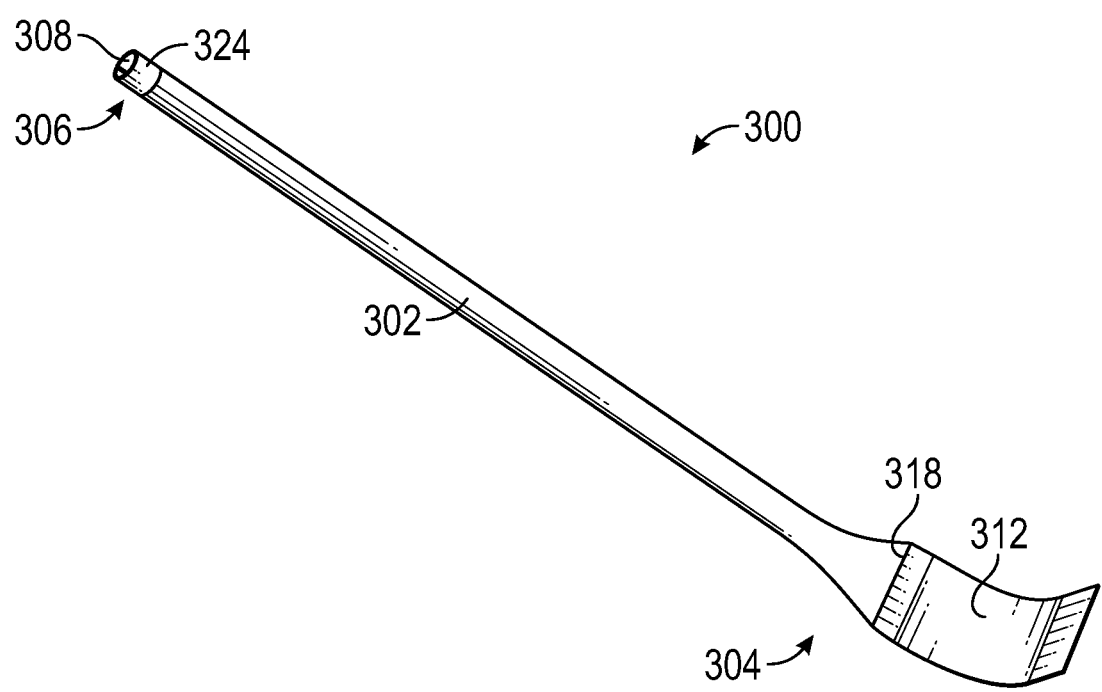
FIGS. 10A-10B are perspective views of an inserter tool to facilitate passing a catheter through a hemostasis valve.
Figure 10B:
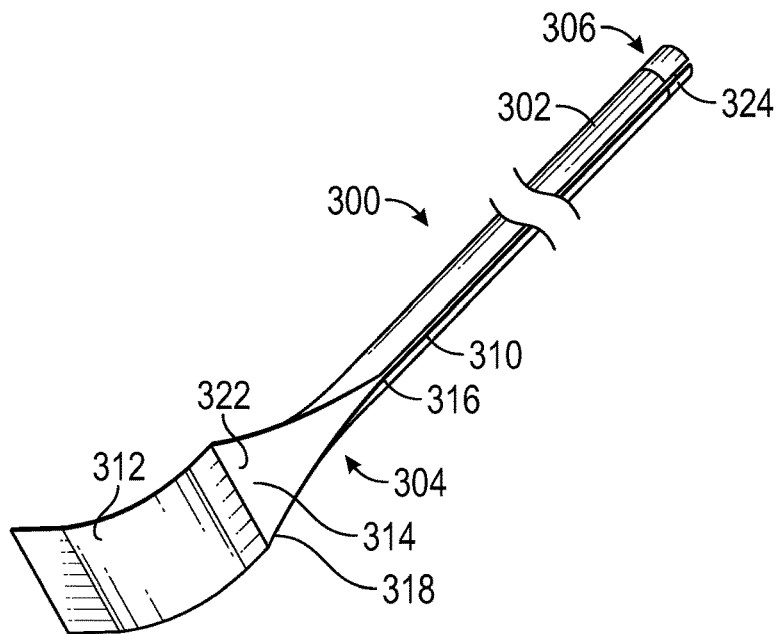
Figure 10C:
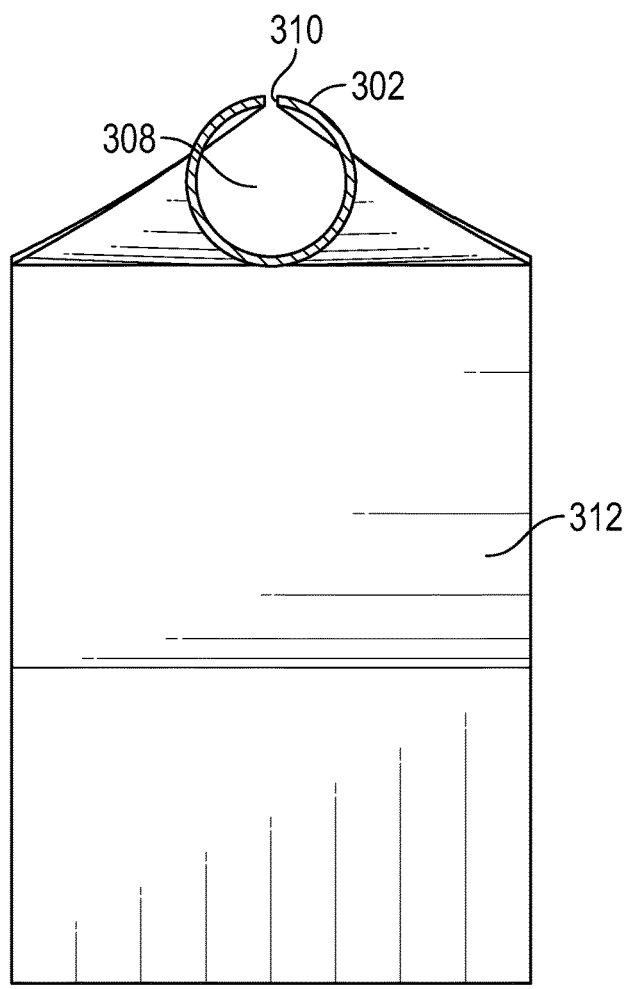
FIG. 10C is an end view of the inserter of FIGS. 10A and 10B.

Referring to FIGS. 10A-10C, there is illustrated a valve inserter in accordance with another embodiment. The inserter enables opening a valve (e.g., the hemostasis valve and/or an introducer sheath valve having an elastomeric membrane valve with a passive slit) and supporting it in an open configuration while providing an access lumen therethrough to enable a delicate secondary device such as a thrombus engagement tool or a catheter to advance therethrough without encountering any resistance or damage from the valve.

The inserter 300 comprises an elongate tubular body 302 having a proximal end 304, a distal end 306, and a central lumen 308 extending therethrough. The tubular body 302 has an inside diameter sufficient to accommodate the secondary device, and an OD capable of passing through a compatible hemostasis valve. In general, tubular body will have an outside diameter within the range of from about 0.04" to about 0.1, and a length within the range of from about 1" to about 4". Tubular body 302 can be formed as an extrusion from any of a variety of common catheter polymers such as Nylon, PEEK, polyethylene, polyimide or others known in the art having sufficient crush resistance and column strength to enter and to maintain patency under the closing pressure of a hemostasis valve.

The proximal end 304 of the tubular body 302 may be provided with a funnel shaped landing zone 322 leading to the central lumen, to facilitate introducing the distal tip of the secondary device into the inserter. In the illustrated embodiment, the proximal end of the tubular body is provided with an inclined face 314. A distal, leading edge 316 of the inclined face 314 is axially distally spaced apart from the trailing proximal edge 318 of the face 314 by a distance D. The distance D [between 316 and 318] may be at least about 0.1" and typically no more than about 0.5".

The inclined face cooperates with the curved sidewall of the tube to create a side opening for funneling the distal tip of the secondary device into the proximal end of the lumen. For this purpose, the side wall at the trailing edge 318 may be provided with a curvature having a greater radius than the radius of curvature at the leading edge 316 with a progressively changing radius in between, creating a funnel shape for the landing zone 322.

The tubular body 302 is provided with an axially extending slit 310 extending between the distal end 306 and the leading edge 316 of the inclined face 314, to enable the inserter to be peeled away laterally from the secondary device extending therethrough once the inserter has enabled passage of the secondary device through the hemostasis valve.

A pull tab 312 may be provided on the proximal end of the tubular body 302 to enable the inserter 300 to be grasped and pulled away from the secondary device extending therethrough. The pull tab 312 may be integrally formed with the tubular body 302 (e.g., as a portion of the sidewall of the tube stock as illustrated) or attached thereto such as by adhesive bonding or mechanical compression or interference engagement. In the illustrated embodiment, the pull tab 312 inclines laterally away from the longitudinal axis of the tubular body, to allow coaxial approach and introduction of the catheter into the inserter 300.

In one implementation of the inserter, the tubular body has a substantially constant diameter throughout most (e.g., at least about 80% or 90%) of its length overall. However, at least the outside diameter in a distal nose segment 324 may be necked down to a smaller outside diameter at the distal end. This enables the inserter to better enter the hemostasis valve under distal compression. In one example, the tubular body has an 8 French ID along most of its length but necks down to 6 French in the distal nose segment 324. This inserter will facilitate the introduction of either a 6 French or an 8 French catheter through the hemostasis valve, since the 8 French catheter can simply forcibly dilate the necked distal end due to the axial slit 310.

In one implementation, the concave entrance funnel surface of the landing zone 322 may be provided with a visual indicium such as a different color than the outside surface of the tubular body 302, to facilitate visualization of the funnel opening and assist in loading the secondary catheter into the funnel. This may be accomplished by providing a colored coating on either the inside or outside surface of the tube stock, or by forming at least a portion of the tube stock as a coextrusion of dissimilar colored materials.

Example Embodiments

A clot capture module for use in a thrombectomy system, the clot capture module comprising one or more of the following:
a housing;
a clot capture chamber in the housing;
a window in the housing to permit visual inspection of the clot capture chamber;
a filter in the clot capture chamber, the filter being visible through the window, the filter having an upstream surface and a downstream surface;
an incoming flow path configured to direct incoming blood from an aspiration catheter against the upstream surface of the filter;
a normally closed aspiration control valve in the incoming flow path, the aspiration control valve configured to block flow of incoming aspirated blood until actuated to permit inflow of aspirated blood; and
an outgoing flow path configured to direct blood from a downstream side of the filter to a remote vacuum canister.

A clot capture module as described in any embodiment herein, further comprising a normally closed vent being openable to permit air to be drawn into the clot capture chamber.

A clot capture module as described in any embodiment herein, wherein the upstream surface of the filter is visible through the window.

A clot capture module as described in any embodiment herein, wherein the upstream surface of the filter is substantially planar.

A clot capture module as described in any embodiment herein, wherein the upstream surface of the filter is convex.

A clot capture module as described in any embodiment herein, wherein the filter comprises a blood permeable membrane, and wherein the upstream surface of the filter is on a radially outwardly facing surface of the blood permeable membrane.

A clot capture module as described in any embodiment herein, wherein the blood permeable membrane at least partially encloses a filtered blood chamber which is in fluid communication with the outgoing flow path.

A clot capture module as described in any embodiment herein, wherein the window comprises a transparent tubular portion of the housing.

A clot capture module as described in any embodiment herein, further comprising an aspiration actuator, configured to control the aspiration control valve.

A clot capture module as described in any embodiment herein, wherein the aspiration actuator comprises a rocker switch.

A clot capture module as described in any embodiment herein in combination with a vacuum line leading to an aspiration pump and canister, wherein the clot capture module is configured to reside within a sterile field while the aspiration pump and canister reside outside of the sterile field.

A clot capture module as described in any embodiment herein, wherein the vacuum line is at least about 30 inches in length.

A clot capture module as described in any embodiment herein, wherein the aspiration control valve comprises collapsible tubing.

A clot capture module as described in any embodiment herein, further comprising a selector valve in the vacuum line.

A clot capture module as described in any embodiment herein, wherein the aspiration pump comprises a syringe.

A clot capture module as described in any embodiment herein, comprising a proximal housing, and a distal housing separated by a transparent tubular side wall.

A clot capture module as described in any embodiment herein, wherein at least one of the proximal housing and distal housing is releasably connected to the transparent tubular side wall.

A clot capture module as described in any embodiment herein, further comprising a coating to inhibit blood accumulation on an interior surface of the window.

A thrombus engagement tool configured to be advanced through a catheter and to engage thrombus, the thrombus engagement tool comprising one or more of the following:
a rotatable core having a proximal end and a distal end; and
a thrombus engagement tip on the distal end of the rotatable core, the thrombus engagement tip comprising:
a helical thread;
an advance segment on a distal side of the helical thread; and
a trailing segment on a proximal side of the helical thread.

A thrombus engagement tool as described in any embodiment herein, further comprising a projection carried by the rotatable core, the projection being underneath at least one of the advance segment and the trailing segment to form an interference fit with the thrombus engagement tip.

A thrombus engagement tool as described in any embodiment herein, wherein the projection comprises an annular ring.

A thrombus engagement tool as described in any embodiment herein, wherein the projection comprises a radiopaque marker.

A thrombus engagement tool as described in any embodiment herein, comprising a first radiopaque marker under the advance segment and a second radiopaque marker under the trailing segment.

A thrombus engagement tool as described in any embodiment herein, wherein an outer periphery of the helical thread substantially conforms to a surface of a cylinder.

A thrombus engagement tool as described in any embodiment herein, wherein the helical thread comprises a proximal surface which inclines radially outwardly in a proximal direction to define a proximally opening undercut.

A thrombus engagement tool as described in any embodiment herein, further comprising a handle on the proximal end of the rotatable core.

A thrombus engagement tool as described in any embodiment herein, comprising a limit bearing surface on the handle, the limit bearing surface being configured to limit projection of the thrombus engagement tip in a distal direction relative to a distal end of the aspiration catheter.

A thrombus engagement tool as described in any embodiment herein, wherein the advance segment, the helical thread, and the trailing segment are all molded onto the rotatable core.

A thrombus engagement tool as described in any embodiment herein, wherein the rotatable core is cannulated.

A thrombus engagement tool as described in any embodiment herein, wherein the rotatable core is a solid wire.

A thrombus engagement tool as described in any embodiment herein, wherein the advance segment comprises an atraumatic tip.

A thrombus engagement tool as described in any embodiment herein, wherein the atraumatic tip comprises a soft polymer.

A thrombus engagement tool as described in any embodiment herein, wherein the handle further comprises an indicium of rotational direction.

A thrombus engagement tool as described in any embodiment herein, wherein the thrombus engagement tip has an axial length within the range of from about 15 mm to about 30 mm.

A thrombus engagement tool as described in any embodiment herein in combination with a catheter having an inside diameter, wherein an outside diameter of the helical thread is no more than about 60% of the inside diameter of the catheter.

A thrombus engagement tool as described in any embodiment herein, wherein the outside diameter of the helical thread is no more than about 40% of the inside diameter of the catheter.

A thrombus engagement tool as described in any embodiment herein, further comprising a position indicator carried by the rotatable core.

A thrombus engagement tool as described in any embodiment herein, wherein the position indicator comprises a distal end of a tube surrounding the rotatable core.

A method of removing embolic material from a vessel with mechanical and aspiration assistance, the method comprising one or more of the following:

providing an aspiration catheter having a central lumen and a distal end;

advancing the distal end to obstructive material in a vessel;

applying vacuum to the central lumen to draw clot into the central lumen;

introducing a thrombus engagement tool into the central lumen, the thrombus engagement tool having a tip comprising a helical thread having a major diameter that is at least about 0.015 inches smaller than an inside diameter of the central lumen, the helical thread being configured to provide an aspiration flow path around the tip; and manually manipulating the tip to engage clot between the tip and an inside wall of the central lumen.

A method of removing embolic material as described in any embodiment herein, wherein the tip is carried by a rotatable core having a proximal handle.

A method of removing embolic material as described in any embodiment herein, wherein the rotatable core is cannulated.

A method of removing embolic material as described in any embodiment herein, wherein the rotatable core is a microcatheter.

A method of removing embolic material as described in any embodiment herein, wherein the rotatable core is a wire.

A method of removing embolic material as described in any embodiment herein, wherein the axial length of the threaded portion of the tip is within the range of from about 5 mm to about 15 mm.

A method of removing embolic material as described in any embodiment herein, further comprising the step of introducing the catheter via a femoral artery prior to the advancing step.

A method of removing embolic material as described in any embodiment herein, comprising the step of advancing the catheter to a pulmonary embolism.

A method of removing embolic material as described in any embodiment herein, comprising the step of advancing the catheter to a deep venous thrombosis.

A method of removing embolic material as described in any embodiment herein, comprising the step of introducing a thrombus engagement tool having a tip with a major diameter that is no more than about 60% of the inside diameter of the central lumen.

A method of removing embolic material as described in any embodiment herein, comprising introducing a thrombus engagement tool having a tip with a major diameter that is no more than about 40% of the inside diameter of the central lumen.

A method of removing embolic material as described in any embodiment herein, wherein the tip is laterally displaced within the central lumen in response to the ingestion of clot.

A method of removing embolic material as described in any embodiment herein, wherein an outer profile of the threaded tip in an end view is substantially circular.

A method of removing embolic material as described in any embodiment herein, wherein the thread has a proximal face and a distal face, and the proximal face inclines radially outwardly in a proximal direction.

A method of removing embolic material as described in any embodiment herein further comprising axially reciprocating the thrombus engagement tool within the catheter.

A method of removing embolic material as described in any embodiment herein, further comprising axially extending the tip beyond the distal end of the catheter.

A method of removing embolic material as described in any embodiment herein, comprising extending the distal tip at least about 2 cm beyond the distal end of the catheter.

A method of removing embolic material as described in any embodiment herein, comprising axially aligning the distal tip with the distal end of the catheter using a position indicator on the rotatable core.

A method of removing embolic material as described in any embodiment herein, further comprising advancing the thrombus engagement tool through a rotating hemostasis valve before introducing the thrombus engagement tool into the central lumen.

A method of removing embolic material as described in any embodiment herein, wherein the position indicator provides haptic feedback as the position indicator passes through the hemostasis valve.

An inserter for guiding a device through a valve, the inserter comprising one or more of the following:
an elongate tubular body having a proximal end, a distal end, and a sidewall at least partially defining a central lumen;
a laterally facing concave landing zone on the proximal end, the concave landing zone having a radius of curvature that increases in a proximal direction; and
an axially extending slit in the sidewall, the axially extending slit extending from the distal end to the concave landing zone.

An inserter as described in any embodiment herein, further comprising a tapered distal tip.

An inserter as described in any embodiment herein, further comprising a pull tab.

An inserter as described in any embodiment herein, wherein a surface of the concave landing zone comprises a different color than an outside surface of the elongate tubular body.

A method of passing a device through a valve, the method comprising one or more of the following:
providing an inserter having a tubular body with a split sidewall;
advancing the tubular body through a valve;
advancing a device through the tubular body and beyond the valve; and
proximally retracting the tubular body so that the device escapes laterally from the tubular body through the split sidewall, leaving the device in place across the valve.

A method of passing a device through a valve as described in any embodiment herein, wherein advancing the tubular body through the valve comprises advancing a tapered distal tip on the tubular body through the valve.

A method of passing a device through a valve as described in any embodiment herein, wherein advancing the tubular body through the valve is accomplished with the device pre loaded inside the tubular body.

A method of passing a device through a valve as described in any embodiment herein, wherein a distal nose segment of the tubular body expands in diameter in response to advancing the device therethrough.

A method of passing a device through a valve as described in any embodiment herein, wherein the device is a thrombus engagement tool.

A method of passing a device through a valve as described in any embodiment herein, wherein the device is a secondary catheter.

A method of passing a device through a valve as described in any embodiment herein, wherein the device is an aspiration catheter.

What is claimed is:

1. A thrombus engagement tool configured to be advanced through a catheter and to engage thrombus, the thrombus engagement tool comprising:
a rotatable core having a proximal end and a distal end; and
a thrombus engagement tip on the distal end of the rotatable core, the thrombus engagement tip comprising:
a helical thread;
an advance segment on a distal side of the helical thread, the advance segment comprising an atraumatic tip, the atraumatic tip comprising a soft polymer; and
a trailing segment on a proximal side of the helical thread.

2. A thrombus engagement tool as in claim 1, further comprising a projection carried by the rotatable core, the projection being underneath at least one of the advance segment and the trailing segment to form an interference fit with the thrombus engagement tip.

3. A thrombus engagement tool as in claim 2, wherein the projection comprises an annular ring.

4. A thrombus engagement tool as in claim 3, wherein the projection comprises a radiopaque marker.

5. A thrombus engagement tool as in claim 4, comprising a first radiopaque marker under the advance segment and a second radiopaque marker under the trailing segment.

6. A thrombus engagement tool as in claim 1, wherein an outer periphery of the helical thread substantially conforms to a surface of a cylinder.

7. A thrombus engagement tool as in claim 6, wherein the helical thread comprises a proximal surface which inclines radially outwardly in a proximal direction to define a proximally opening undercut.

8. A thrombus engagement tool as in claim 1, further comprising a handle on the proximal end of the rotatable core.

9. A thrombus engagement tool as in claim 8, comprising a limit bearing surface on the handle, the limit bearing surface being configured to limit projection of the thrombus engagement tip in a distal direction relative to a distal end of an aspiration catheter.

10. A thrombus engagement tool as in claim 8, wherein the handle further comprises an indicium of rotational direction.

11. A thrombus engagement tool as in claim 1, wherein the advance segment, the helical thread, and the trailing segment are all molded onto the rotatable core.

12. A thrombus engagement tool as in claim 1, wherein the rotatable core is cannulated.

13. A thrombus engagement tool as in claim 1, wherein the rotatable core is a solid wire.

14. A thrombus engagement tool as in claim 1, wherein the thrombus engagement tip has an axial length within a range of from about 15 mm to about 30 mm.

15. A thrombus engagement tool as in claim 1 in combination with a catheter having an inside diameter, wherein an outside diameter of the helical thread is no more than about 60% of the inside diameter of the catheter.

16. A thrombus engagement tool as in claim 15, wherein the outside diameter of the helical thread is no more than about 40% of the inside diameter of the catheter.

17. A thrombus engagement tool as in claim 1, further comprising a position indicator carried by the rotatable core.

18. A thrombus engagement tool as in claim 17, wherein the position indicator comprises a distal end of a tube surrounding the rotatable core.

19. A thrombus engagement tool configured to be advanced through a catheter and to engage thrombus, the thrombus engagement tool comprising:

a rotatable core having a proximal end and a distal end;

a thrombus engagement tip on the distal end of the rotatable core, the thrombus engagement tip comprising:
   a helical thread;
   an advance segment on a distal side of the helical thread; and
   a trailing segment on a proximal side of the helical thread; and a handle on the proximal end of the rotatable core, the handle comprising an indicium of rotational direction.

20. A thrombus engagement tool as in claim 19, further comprising a projection carried by the rotatable core, the projection being underneath at least one of the advance segment and the trailing segment to form an interference fit with the thrombus engagement tip.

21. A thrombus engagement tool as in claim 20, wherein the projection comprises an annular ring.

22. A thrombus engagement tool as in claim 21, wherein the projection comprises a radiopaque marker.

23. A thrombus engagement tool as in claim 22, comprising a first radiopaque marker under the advance segment and a second radiopaque marker under the trailing segment.

24. A thrombus engagement tool as in claim 19, wherein an outer periphery of the helical thread substantially conforms to a surface of a cylinder.

25. A thrombus engagement tool as in claim 24, wherein the helical thread comprises a proximal surface which inclines radially outwardly in a proximal direction to define a proximally opening undercut.

26. A thrombus engagement tool as in claim 19, comprising a limit bearing surface on the handle, the limit bearing surface being configured to limit projection of the thrombus engagement tip in a distal direction relative to a distal end of an aspiration catheter.

27. A thrombus engagement tool as in claim 19, wherein the advance segment, the helical thread, and the trailing segment are all molded onto the rotatable core.

28. A thrombus engagement tool as in claim 19, wherein the rotatable core is cannulated.

29. A thrombus engagement tool as in claim 19, wherein the rotatable core is a solid wire.

30. A thrombus engagement tool as in claim 19, wherein the advance segment comprises an atraumatic tip.

31. A thrombus engagement tool as in claim 19, wherein the thrombus engagement tip has an axial length within a range of from about 15 mm to about 30 mm.

32. A thrombus engagement tool as in claim 19 in combination with a catheter having an inside diameter, wherein an outside diameter of the helical thread is no more than about 60% of the inside diameter of the catheter.

33. A thrombus engagement tool as in claim 32, wherein the outside diameter of the helical thread is no more than about 40% of the inside diameter of the catheter.

34. A thrombus engagement tool as in claim 1, further comprising a position indicator carried by the rotatable core.

35. A thrombus engagement tool as in claim 34, wherein the position indicator comprises a distal end of a tube surrounding the rotatable core.

* * * * *